United States Patent [19]

Clemence et al.

[11] Patent Number: 5,063,225
[45] Date of Patent: Nov. 5, 1991

[54] BENZOTHIAZEPINES

[75] Inventors: Francois Clemence; Daniel Fréchet, both of Paris; Gilles Hamon, Le Raincy; Simone Jouquey, Paris, all of France

[73] Assignee: Roussel Uclaf, Paris, France

[21] Appl. No.: 508,127

[22] Filed: Apr. 11, 1990

[30] Foreign Application Priority Data

Apr. 13, 1989 [FR] France .................. 89 04905

[51] Int. Cl.$^5$ ................. C07D 281/10; C07D 417/06; A61K 31/55
[52] U.S. Cl. .................. 514/211; 540/491
[58] Field of Search .............. 540/491; 514/211

[56] References Cited

U.S. PATENT DOCUMENTS 3,075,967  1/1963  Krapcho ............. 540/491

*Primary Examiner*—Robert T. Bond
*Attorney, Agent, or Firm*—Bierman and Muserlian

[57] ABSTRACT

A compound selected from the group consisting of all possible isomeric forms, racemic or optically active of a compound of the formula

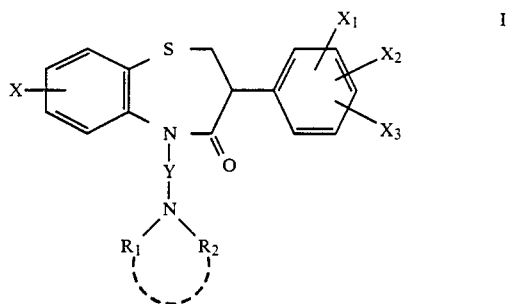

wherein the substituents are defined in the specification, and their non-toxic, pharmaceutically acceptable acid addition salts having antiarhythmic activity.

25 Claims, No Drawings

BENZOTHIAZEPINES

STATE OF THE ART

Related prior art includes U.S. Pat. Nos. 3,330,823 and 3,075,967, European patent application No. 0,262,373 and European Journal of Medicinal Chemistry, Vol. 9, No. 4, 1979, page 376 to 380.

OBJECTS OF THE INVENTION

It is an object of the invention to provide the novel benzothiazepines of formula I and their non-toxic, pharmaceutically acceptable acid addition salts and a novel process and novel intermediates for their preparation.

It is another object of the invention to provide novel antiarhythmic compositions and a novel method of treating arhythmia in warm-blooded animals.

These and other objects and advantages of the invention will become obvious from the following detailed description.

THE INVENTION

The novel compounds of the invention are selected from the group consisting of all possible isomeric forms, racemic or optically active of a compound of the formula

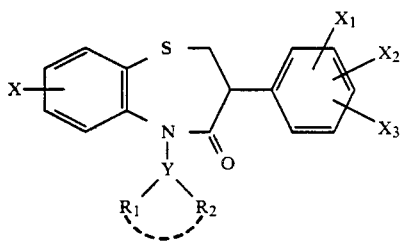

wherein X is selected from the group consisting of hydrogen, halogen, —OH, alkyl and alkoxy of 1 to 3 carbon atoms, —$NO_2$, —$NH_2$, —$CF_3$ and alkylamino and dialkylamino of 1 to 4 alkyl carbon atoms, $X_1$, $X_2$ and $X_3$ are individually selected from the group consisting of hydrogen, halogen, —OH, alkyl and alkoxy of 1 to 3 carbon atoms, —$NO_2$, —$CF_3$, —$SCF_3$, —$OCF_3$, —$NH_2$ and alkylamino and dialkylamino of 1 to 4 alkyl carbon atoms, Y is

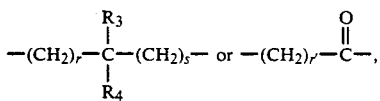

r and s are integers from 0 to 4 with r+s=1 to 4, $R_3$ and $R_4$ are individually hydrogen or alkyl of 1 to 4 carbon atoms, r' is an integer from 1 to 4, $R_1$ and $R_2$ are individually selected from the group consisting of hydrogen, alkyl of 1 to 4 carbon atoms unsubstituted or substituted with aryl of 6 to 12 carbon atoms optionally substituted with 1 to 3 members of the group consisting of alkyl and alkoxy of 1 to 4 carbon atoms, —OH, —CN, halogen, —$NH_2$ and alkylamino and dialkylamino of 1 to 4 alkyl carbon atoms or $R_1$ and $R_2$ together with the nitrogen to which they are attached form a 5 to 7 member saturated heterocycle optionally containing —S—, —O— or another nitrogen atom optionally substituted and their non-toxic, pharmaceutically acceptable acid addition salts.

The halogen may be fluorine, bromine or iodine but preferably chlorine. Examples of alkyl and alkoxy are methyl, ethyl, propyl, isopropyl, butyl, isobutyl, sec.-butyl, tert.-butyl, methoxy, ethoxy, propoxy, isopropoxy, n-butoxy, isobutoxy sec.-butoxy and tert.-butoxy. Examples of monoalkylamino and dialkylamino are methylamino, ethylamino, isopropylamino, dimethylamino, methylethylamino, diethylamino, dipropylamino and diisopropylamino.

Examples of saturated heterocyclics with five, six or seven links that $R_1$ and $R_2$ can form with the nitrogen atom to which they are linked optionally with another heteroatom chosen from the following atoms: nitrogen, oxygen or sulfur, include pyrrolidinyl, imidazolidinyl, pyrazolidinyl, piperidyl, piperazinyl or morphlinyl. The said radicals can be optionally substituted on a carbon of the heterocycle or on the nitrogen atom when the heterocycle contains a second nitrogen atom by alkyl of 1 to 4 carbon atoms or by aryl or arylalkyl of 6 to 12 carbon atoms optionally substituted with 1, 2 or 3 members of the group consisting of halogen and alkyl or alkoxy of 1 to 4 carbon atoms. Aryl preferably includes phenyl and arylalkyl preferably includes benzyl or phenethyl. Among the aryl or arylalkyl substituents are halogen, methyl, ethyl, methoxy, ethoxy or propoxy preferably.

The salification of the products can be effected by standard methods with mineral acids such as hydrochloric acid, hydrobromic acid, nitric acid, phosphoric acid or sulfuric acid; organic acids such as formic acid, acetic acid, acrylic acid, butyric acid, adipic acid, glutaric acid, crotonic acid, propionic acid, benzoic acid, maleic acid, fumaric acid, succinic acid, tartaric acid, citric acid, oxalic acid, glyoxylic acid, aspartic acid, hexanoic acid, heptanoic acid, decanoic acid, oleic acid, stearic acid, palmitic acid, isobutylic acid, (4-methyl pentanoic acid), chloropropionic acid, phenylacetic acid, 2-thiophenacetic acid, 3-thiophenacetic acid, (4-ethylphenyl) acetic acid, the monoethyl ester of adipic acid, 3-hydroxypropionic acid, 3-methoxy propionic acid, 3-methylthiobutyric acid, 4-chloro butyric acid, 4-phenyl butyric acid, 3-phenoxy butyric acid, 4-ethyl benzoic acid, 1-propyl benzoic acid and alkanesulfonic acids such as methane or ethane sulfonic acid and arylsulfonic acids such as benzene sulfonic acid.

Among the preferred compounds of formula I are those wherein X is hydrogen, those wherein $R_1$ and $R_2$ are both methyl, ethyl or isopropyl, those wherein $R_1$ is methyl and $R_2$ is phenethyl optionally mono- or di-substituted with methyl or methoxy, those wherein $R_1$ is hydrogen and $R_2$ is dialkylaminomethyl or dialkylaminoethyl, those wherein $R_1$ and $R_2$ form together with the nitrogen atom to which they are attached pyrrolidinyl, piperidyl, morpholinyl or piperazinyl optionally substituted on the nitrogen atom that is not linked to the —$(CH_2)_s$— with alkyl of 1 to 4 carbon atoms or aryl or arylalkyl of 6 to 12 carbon atoms optionally substituted by halogen or alkyl or alkoxy of 1 to 4 carbon atoms as well as their addition salts with mineral or organic acids. When $R_1$ and $R_2$ form piperazinyl, it may be substituted with methyl, methoxymethyl, phenyl or methylphenyl.

Other preferred compounds of formula I are those wherein $X_3$ is hydrogen and $X_1$ and $X_2$ are individually chlorine, bromine, —OH or methoxy, those wherein Y is

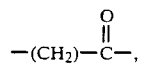

those wherein Y is —(CH$_2$)$_r$—CH$_2$(CH$_2$)$_s$— and r+s is 1 or 2 and their non-toxic, pharmaceutically acceptable acid addition salts.

Examples of specific preferred compounds of the invention are (±)-5-[2-(dimethylamino)-ethyl]-2,3-dihydro-3-(4-chlorophenyl)-1,5-benzothiazepin-4(5H)-one; (±)-5-[2-(dimethylamino)-ethyl]-2,3-dihydro-3-(2-methoxy-phenyl)-1,5-benzothiazepin-4(5H)-one; (±)-5-[2-(dimethylamino)-ethyl]-2,3-dihydro-3-(4-methoxy-phenyl)-1,5-benzothiazepin-4-(5H)-one and their addition salts with mineral or organic acids.

The novel process of the invention for the preparation of the compounds of formula I wherein Y is

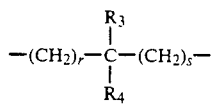

comprises reacting an optical isomer or racemic mixture of a compound of the formula

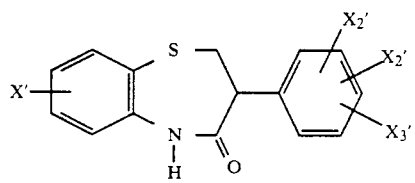

wherein X' is X or a protected reactive group, X$_1$', X$_2$' and X$_3$' are X$_1$, X$_2$ and X$_3$ respectively or protected reactive groups thereof either with a compound of the formula

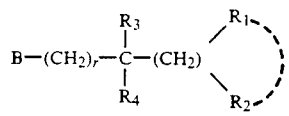

wherein R$_1$, R$_2$, R$_3$, R$_4$, r and s have the above definitions and B is halogen or —OH to obtain a compound of the formula

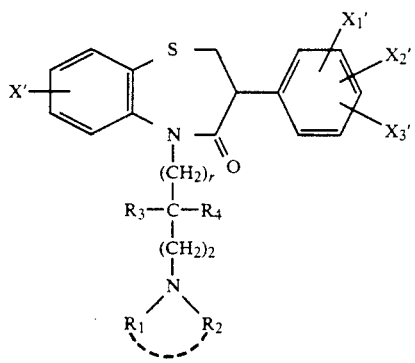

or with a product of the formula

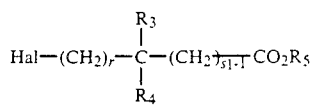

wherein R$_3$, R$_4$ and r have the above definitions, s$_1$ is an integer from 1 to 4, Hal is halogen and R$_5$ is alkyl of 1 to 4 carbon atoms to obtain a compound of the formula

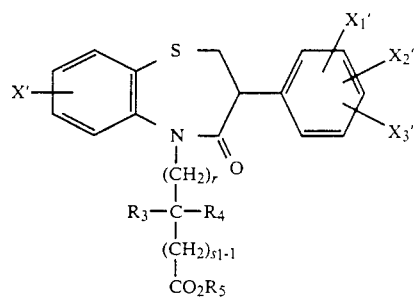

subjecting the latter to a hydrolysis reaction to obtain a compound of the formula

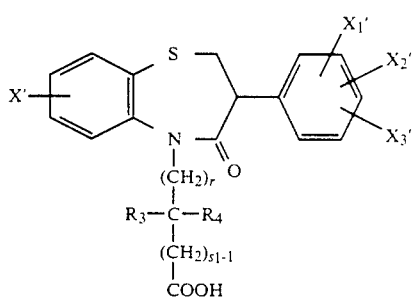

subjecting the latter to a reduction to obtain a product of the formula

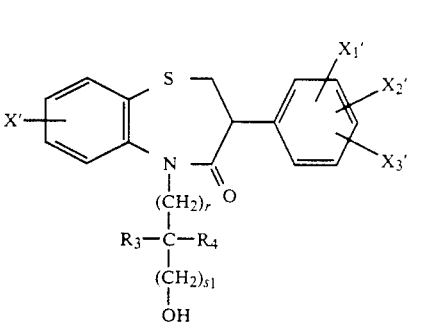

subjecting the latter to a substitution reaction with a halogen to obtain a product of the formula

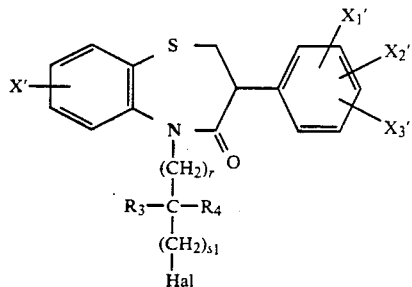
VIII reacting the latter with an amine of the formula

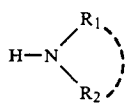
IX to obtain a product of the formula

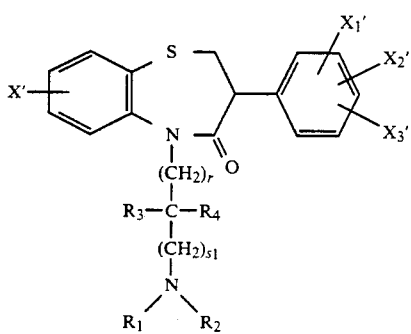
XI

The process of the invention to form the compounds of formula I wherein Y is

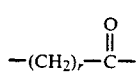

comprises reacting a compound of formula II with either a compound of the formula

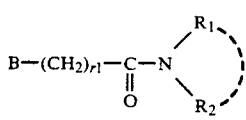
III' wherein B, $r_1$, $R_1$ and $R_2$ have the above definitions to obtain a compound of the formula

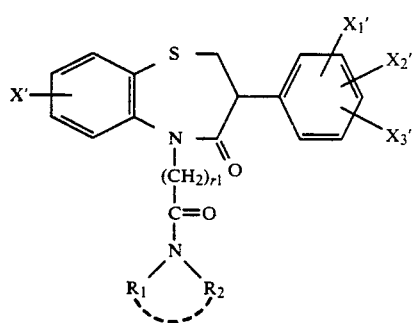
XVII or with a compound of the formula

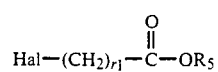
XVII:

wherein $R_5$ and $r_1$ have the above definitions to obtain a compound of the formula

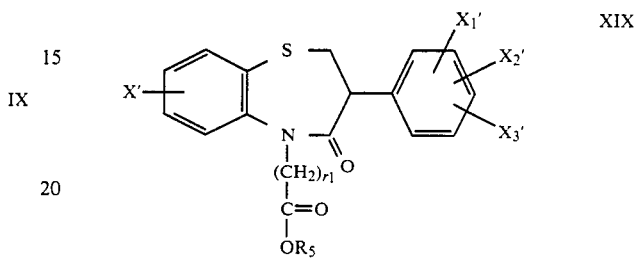
XIX and hydrolyzing the latter to obtain a compound of the formula

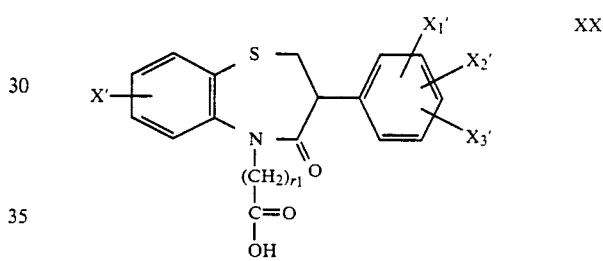
XX and reacting the latter with an amine of formula IX to obtain a compound of formula XVII and optionally reacting the compounds of formulae X, XI and XVII to at least one of the following reactions in any order; a) removal of the protective group of any protected groups by hydrolysis or hydrogenolysis; b) resolution by standard procedures of racemates and c) salification with an acid to form the acid addition salts.

Examples of protective groups for amino and monoalkylamino of X', $X_1'$, $X_2'$ or $X_3'$ are alkyl of 4 to 6 carbon atoms, preferably tert.-butyl or tert.-pentyl, an aliphatic, aromatic or heterocyclic acyl or a carbamoyl such as lower alkanoyl like formyl, acetyl, propionyl, butyryl, benzoyl, isobutyryl, valeryl, isovaleryl, oxalyl, succinyl and pivaloyl and substituted acyl such as chloroacetyl; a lower alkoxy or cycloalkoxycarbonyl such as methoxycarbonyl, ethoxycarbonyl, propoxycarbonyl, (1-cyclopropyl ethoxycarbonyl), isopropyloxycarbonyl, butyloxycarbonyl, tert.-butyloxycarbonyl, pentyloxycarbonyl, hexyloxycarbonyl; lower arylalkyl such as benzyl, 4-methoxybenzyl, phenylethyl, trityl, (3,4-dimethoxy benzyl) or benzhydryl; haloalkyl such as trichloroethyl; chlorobenzoyl, p-nitro-benzoyl, p-tert.-butyl benzoyl, phenoxyacetyl, decanoyl, acryloyl, trichloroethoxycarbonyl; methylcarbamoyl, phenylcarbamoyl, naphthylcarbamoyl as well as the corresponding thiocarbamoyls. The above list is not limitative and it will be obvious that other amine protector groups, known groups in particular in the chemistry of the peptides, can also be used.

Examples of the protective group for protected hydroxyl of X′, X₁′, X₂′ or X₃′ are acyl such as formyl, acetyl, chloroacetyl, bromoacetyl, dichloroacetyl, trichloroacetyl, trifluoroacetyl, methoxyacetyl, phenoxyacetyl, benzoyl, benzoylformyl, p-nitro benzoyl; ethoxycarbonyl, methoxycarbonyl, propoxycarbonyl, (2,2,2-trichloro-ethoxy) carbonyl, benzyloxycarbonyl, tert.-butoxycarbonyl, (1-cyclopropyl-ethoxy) carbonyl, tetrahydropyrannyl, tetrahydrothiopyrannyl, methoxytetrahydropyrannyl, trityl, benzyl, 4-methoxy benzyl, benzhydryl, trichloroethyl, (1-methyl-1-methoxy-ethyl) and phthaloyl.

Other acyls include propionyl, butyryl, isobutyryl, valeryl, isovaleryl, oxalyl, succinyl, and pivaloyl. Also useful are phenylacetyl, phenylpropionyl, mesyl, chlorobenzoyl, para-nitrobenzoyl, p-(tert.-butyl) benzoyl, acryloyl, methyl-carbamoyl and phenylcarbamoyl.

In a preferred mode of the process of the invention, B of the compound of formula III is —OH or chlorine and in the compound of formula III′ is bromine or chlorine. The reaction of the compounds of formulae II and III when B is —OH is effected in the presence of diethyl azodicarboxylate, triphenylphosphine, dicyclohexylcarbodiimide—and particularly in an ether which is preferably ethyl ether or tetrahydrofuran or dioxane. The reaction takes place over a time span of 4 to 24 hours at ambient temperature. When B is a halogen, the reaction is effected in the presence of a base which can be sodium hydroxide or preferably sodium hydride in dimethylformamide for a period on the order of 4 hours at a temperature of about 60° C.

In the compounds of formulae IV or XVIII, the halogen can be bromine but also chlorine, iodine or fluorine. The reaction of the compound of formulae IV or XVIII with the compound of formula II is carried out in the presence of a mineral base, preferably sodium hydride and the hydrolysis of the ester of formulae V or XIX in the acid of formulae VI or XX is carried out in an acid medium, preferably aqueous sulfuric acid in the presence of acetic acid, but also with hydrochloric acid or aqueous hydrobromic acid. The selective reduction of the acid of formula VI in the alcohol of formula VII is carried out preferably in the presence of a diborane complex or lithium aluminum hydride or diisobutylaluminum hydride. The preparation of the halogen derivative of formula VIII is carried out advantageously by the action of thionyl chloride in dichloromethane for a period of several minutes at ambient temperature and the addition of the amine of formula IX to the products of formulae VIII or XX is carried out equally well with or without an organic solvent at ambient or high temperature.

Depending on the values of X′, X₁′, X₂′ and X₃′, the products of formulae X, XI and XVII may or may not constitute the products of formula I. The products of formulae X, XI and XVII constitute the products of formula I when X′, X₁′, X₂′ and/or X₃′ are not a protected reactive radical, this reactive radical being hydroxyl, amino or monoalkylamino. In the other cases, the action on the products of formulae X, XI or XVII of one or more hydrolysis or hydrogenolysis agents or thiourea has the object of eliminating the protector group in X′, X₁′, X₂′ or X₃′ when this protects a hydroxyl, amino or monoalkylamino radical. The nature of the reagents employed in such a case is well known to an expert. A non-exhaustive enumeration of the means capable of being employed to eliminate the different groups is given hereafter.

The elimination of the protective group of X′, X₁′, X₂′ and/or X₃′, when the protected function is an amino or monoalkylamino hydroxyl radical can be carried out by acidic hydrolysis. The acid which is preferably used can be chosen from the group consisting of hydrochloric acid, benzene sulfonic acid or p-toluene sulfonic acid, formic acid or trifluoroacetic acid but other mineral or organic acids can be used.

The groups such as trichloroethyl, benzyhydryl, benzyloxycarbonyl are preferably eliminated by hydrogenolysis using zinc-acetic acid or hydrogen in the presence of a catalyst can be cited. The elimination of the chloroacetyl can be carried out by thiourea, for example according to the conditions described in MASAKI, JACS, Vol. 90, p 4508, (1968). Indications on the protector groups and their elimination methods are also given, for example, in the French Patent No. 2,499,995, the contents of which are incorporated into the present application by reference.

Naturally, when X′, X₁′, X₂′ and X₃′ are eliminatable groups belonging to different types, several agents envisaged in the previous enumerations can be reacted on the products. The salification of the products can be carried out according to standard methods using one of the mineral or organic acids chosen from the above list.

The novel antiarhythmic compositions of the invention are comprised of an antiarhythmically effective amount of at least one compound of formula I and its non-toxic, pharmaceutically acceptable acid addition salts and an inert pharmaceutical carrier. The compositions may be in the form of tablets, dragees, capsules, granules, suppositories, creams, gels, ointments, injectable solutions and suspensions.

Examples of suitable excipients are talc, gum arabic, lactose, starch, magnesium stearate, cocao butter, aqueous or non-aqueous vehicles, animal or vegetable fatty substances, paraffin derivatives, glycols, various wetting, dispersing or emulsifying agents and preservatives.

The compositions besides their antiarhythmic activity also possess, anti-aggregation of blood platelets, and anti-serotoninergic properties and certain of the compounds of formula I show an anti-calcic activity.

The anti-rhythmic properties of the compositions allow the treatment of cardiac rhythm disturbances. Their anti-calcic effect combined with their properties pertaining to anti-aggregation of blood platelets and their anti-serotoninergic properties make them active in the treatment of angina pectoris as well as in the case of spastic angina as of unstable angina. Those properties pertaining to anti-aggregation of blood platelets and anti-serotoninergic properties also mean they can be used in the treatment of migraine attacks or in an anti-thrombosis, preventative role.

The novel method of the inventions for inducing anti-arhythmic activity in warm-blooded animals, including humans, comprises administering to warm-blooded animals or antiarhythmically effective amount of at least one compound of formula I and its non-toxic, pharmaceutically acceptable acid addition salts. The compounds may be administered rectally, buccally, parenterally or topically to the skin or mucous membranes. The usual daily dose is 0,26 to 5,33 mg/kg depending on the condition being treated, the specific compound and method of administration.

The novel intermediates of the invention are those of formulae V, VI, VII, VIII, XIX and XX.

The product of formula II including 3-(2,4-dichlorophenyl)-2,3-dihydro-1,5-benzothiazepin-4-(5)-one and 3-(2,5-dichlorophenyl)-2,3-dihydro-1,5-benzothiazepin-4(5)-one are known [J. Med. Chem., Vol. 8 (3), p. 511 (1971)] and can be prepared starting from a compound of the formula

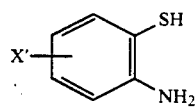
XII and the products of formula

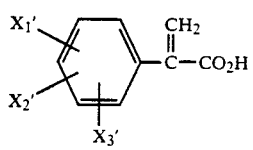
XIII

The products of formula XII are themselves known or can be prepared by standard methods, for example, those described in the following references: LIEBIGS, Ann. Chem., 1987 (11), p. 921 to 925; V.A.R.J. Chem., 1971, Vol. 14 (5), p. 493 to 505; German Patent Application DE 2,368,760 and Japanese Patent Application No. 79/145.678.

The products of formula XIII are known and can be prepared by the method described in the experimental part and in U.S. Pat. No. 3,574,215 which consists of reacting diethyloxalate in toluene in the presence of sodium ethylate with a product of the formula

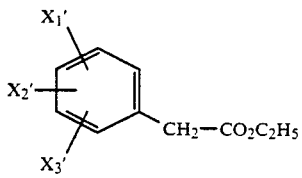
XIV to obtain a product of the formula

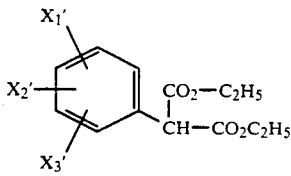
XV which is reacted with formaldehyde in the presence of $K_2CO_3$ to obtain a product of the formula

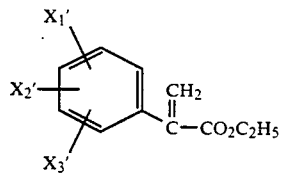
XVI which is subjected to a saponification reaction with potassium hydroxide in a THF-$H_2O$ medium, which allows the product of formula XIII to be obtained. The products of formula XIII can also be prepared by one of the two techniques described respectively in the article EUR. J. Med. Chem. 1979, Vol. 14 (3), page 477 to 480. Certain products of formulae III, III' and IV are known or even available commercially. The products of formula III which are not described can be prepared by methods known to the expert.

Examples of the preparation of the products of formula III are indicated in the following publications: Berichte, Vol. 37, p. 3508 (1904) or J. Chem. Soc. 1927, 1012 cited by the Merck Index 10th edition No. 2825, Beil 20 (2) 5.

Examples of the preparation of products of formula IV are given in "I of PHARMACY and PHARMACOLOGY," 1952, II. p. 61., Beil 2, 325 and Beil 2 (3) 737.

In the following examples there are described several preferred embodiments to illustrate the invention. However, it should be understood that the invention is not intended to be limited to the specific embodiments.

EXAMPLE 1

2,3-dihydro-3-(4-methoxy-phenyl)-5-[2-(1-pyrrolidinyl)-ethyl]-1,5-benzothiazepin-4(5H)-one (Z)-2-butenedioate

STEP A: Methyl 4-methoxy-α-methylene benzeneacetate

A solution of 36 g of methyl 4-methoxy-phenylacetate, 32 g of dimethyl oxalate and 250 ml of ethyl ether was added over 15 minutes to a suspension of 13.8 g of sodium methylate (prepared from 5.9 g of sodium) and 400 ml of ethyl ether and the mixture was stirred for 17 hours at reflux. 200 ml of ether was added, then while cooling, 200 ml of 2N hydrochloric acid were added over 30 minutes. After decanting, the ether phase was washed with 50 ml of 2N hydrochloric acid, then three times with 50 ml of a saturated solution of sodium chloride and brought to dryness under reduced pressure. The residue was taken up in 400 ml of water and 40 ml of 40% formaldehyde and 30.4 g of potassium carbonate were added with a trace of hydroquinone. The mixture was stirred for 3 hours at ambient temperature. After extraction with ethyl acetate and washing with water, the extracts were evaporated to dryness under reduced pressure. The residue was chromatographed on silica (eluant: cyclohexane-ethyl acetate: 95-5) to obtain 26 g of the desired product.

| NMR Spectrum ($CDCl_3$) 60 MHz | |
|---|---|
| the $OCH_3$'s | 227 Hz |
| 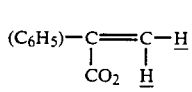 | 348 (d, j approx. 1.5 Hz)<br>375 (d, j approx. 1.5 Hz) |
| aromatics | 408 to 446 Hz. |

STEP B: 4-methoxy-α-methylene bnzeneacetic acid 500 ml of a 25% aqueous solution of potassium hydroxyde were added to a solution of 26 g of the product of Step A in 750 ml of tetrahydrofuran, and the mixture was stirred for 66 hours at ambient temperature. After evaporation of the solvent, 500 ml of water were added and the aqueous phase was washed with ethyl acetate, then acidified with concentrated hydrochloric acid. After separation, 23 g of the desired product melting at 118° C. were obtained and used as is for the next step. An analytical sample was obtained by crystallization of 2 g of the crude product from 150 ml of water to obtain 1.1 g of purified product melting at 118° C.

| IR Spectrum (CHCl₃ on Nicolet) | |
|---|---|
| —C—<br>‖<br>O | 1727 cm⁻¹ (ep.)<br>1697 cm⁻¹ (max.) |
| —C=C<br>+<br>aromatics | 1612 cm⁻¹ (F)<br>1575 cm⁻¹<br>1513 cm⁻¹ (F) |

STEP C:
α-[[(2-amino-phenyl)-thio]-methyl]-4-methoxy benzeneacetic acid

A solution of 125 ml of ethanol, 8.9 g of 4-methoxy-α-methylene benzeneacetic acid and 5.35 ml of 2-amino thiophenol was refluxed for 7 hours. The ethanol was evaporated off and the residue was crystallized from 500 ml of isopropyl ether to obtain 11 g of the desired product melting at 118° C. and used as is for the following step.

An analytical sample was prepared by crystallization of 200 mg of crude product from 20 ml of isopropyl ether to obtain 140 mg of purified product melting at 118° C.

| NMR SPECTRUM (CDCl₃, 60 MHz) | |
|---|---|
| =C—OCH₃ | 3 H approx. 225 Hz |
| 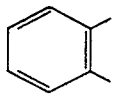 | 4 H approx 387 to 414 Hz |
| 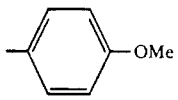—OMe | 4 H 417 to 443 Hz |
| the mobile H's<br>the other H's | approx 3 H 364 Hz<br>168 to 227 Hz |

STEP D:
2,3-dihydro-3-(4-methoxy-phenyl)-1,5-benzothiazepin-4(5H)-one 7 g of dicyclohexylcarbodiimide were added while cooling to a solution of 10.3 g of the product of Step C in 300 ml of ethanol and the mixture was stirred for 17 hours at ambient temperature. The ethanol was evaporated off and the residue was taken up in 150 ml of ethyl acetate. The insoluble part was filtered off and the filtrate was evaporated to dryness under reduced pressure. The residue was taken up in 25 ml of isopropanol and after drying, 5.85 g of the desired product melting at 145° C. were obtained. The filtrate was chromatographed on silica (eluant: cyclohexane-ethyl acetate 5-5) to obtain a further 2.2 g of product which after crystallization from 20 ml of isopropanol melted at 146° C.

Analysis: C₁₆H₁₅NO₂S; molecular weight = 285.352: Calculated: %C, 67.34; %H, 5.30; %N 4.91; %S, 11.23. Found: %C, 67.1; %H, 5.2; %N, 4.7; %S, 11.1.

| IR Spectrum (CHCl₃ on Nicolet) | |
|---|---|
| —NH—C—<br>‖<br>O | { 3387 cm⁻¹<br>{ 1682 cm⁻¹ |
| —OMe | 2838 cm⁻¹ |
| NMR Spectrum (CDCl₃, 90 MHz) | |
| S—CH₂—CH | 203 to 243 Hz |
| —OCH₃ | 226 Hz |
| NH | 478 Hz |
| the aromatic H's | 406 to 465 Hz |

STEP E:
2,3-dihydro-3-(4-methoxy-phenyl)-5-[2-(1-pyrrolidinyl)-ethyl]-1,5-benzothiazepin-4(5H)-one 2.3 g of 1-(2-hydroxy-ethyl)-pyrrolidine were added to a solution of 2.85 g of the product of Step D and 5.25 g of triphenyl phosphine in 100 ml of anhydrous tetrahydrofuran and then over 10 minutes, 3.48 g of diethyl azodicarboxylate in solution in 50 ml of anhydrous tetrahydrofuran were added. The mixture was stirred for 22 hours at ambient temperature and evaporated to dryness under reduced pressure to obtain 15 g of the desired crude product which was chromatographed on silica to obtain 2.61 g of the expected product.

| NMR Spectrum (250 MHz, CDCl₃) | |
|---|---|
|  | 1.78 (m), 2.66 (m) |
| CH₂—N | 2.45 to 3.00 (m) |
| O—CH₃ | 3.77 (s) |
| CH₂—CH (3H) | 3.40 to 4.50 (m) |
| 2H in ortho position of O—CH₃ | 6.82 (d) |
| 2H in meta position of O—CH₃ | 7.25 (d) |
| 3 other aromatic H's | 7.10 to 7.60 (m) |
| H6 integration base | 7.66 (d, 1) |

STEP F: 2,3-dihydro-3-(4-methoxy phenyl)-5-[2-(-1-pyrrolidinyl)-ethyl]-1,5-benzothiazepin-4(5H)-one (Z)-2-butenedioate A solution of maleic acid in stoichiometric quantity in 10 ml of isopropanol was added to a solution of 2.26 g of the product of Step A in 15 ml of isopropanol and the mixture was concentrated to a total volume of 15 ml, left at rest for 8 hours at ambient temperature, and for one night at 0° C. The mixture was separated at ambient temperature, washed with 3 ml of isopropanol and 10 ml of ethyl ether to obtain 1.41 g of product melting at 170° C. 1.4 g of the latter were dissolved in 150 ml of isopropanol at reflux, concentrated to 20 ml, stood at rest for 20 hours at ambient temperature and separated to obtain 1.29 g of desired product melting at 170° C.

Analysis: C₂₆H₃₀N₂O₆S; molecular weight = 498.6: Calculated: %C, 62.63; %H, 6.06; %N, 5.62; %S, 6.43. Found: %C, 62.5; %H, 6.3; %N, 5.5; %S, 6.2.

| NMR Spectrum (CDCl₃, 250 MHz): | |
|---|---|
| 2.08 | H in β position of N-pyrrolidine |
| 3.78 (s) | O—CH₃ |
| from 2.7 to 4.5 (m) | NCH₂—CH₂—N<br>CH in α position of N- |

| NMR Spectrum (CDCl₃, 250 MHz): | |
|---|---|
| 6.23 (s) | pyrrolidine<br>SC$\underline{H}$₂—C$\underline{H}$—(C₆H₅)<br>ethylenics |
| 6.85 (d) | H in ortho position of<br>O—CH₃ |
| 7.21 (d) | H in meta position of<br>O—CH₃ |
| 7.83 (t)<br>7.41 (d)<br>7.57 (t)<br>7.68 (d) | } the other aromatics |

EXAMPLE 2

(±)-3-(3-bromo-4-methoxy-phenyl)-2,3-dihydro-5-[2-(dimethyl-amino)-ethyl]-1,5-benzothiazepin-4-(5H)-one hydrochloride

STEP A:
3-(3-bromo-4-methoxy-phenyl)-2,3-dihydro-1,5-benzothiazepin-4(5H)-one 24 ml of a N solution of bromine in acetic acid were added to a solution of 2.28 g of 2,3-dihydro-3-(4-methoxy phenyl)-1,5-benzothiazepin-4(5H)-one of Step D of Example 1 in 16 ml of acetic acid. After 22 hours of stirring at ambient temperature, 100 ml of essence G were added and the gummy precipitate obtained was separated off by decanting the solution. Then, it was crystallized from 20 ml of ethanol and stirred for 30 minutes, followed by separation to obtain 2.22 g of the desired product melting at 200° C., then 220° C. The product was used as is for the following step. An analytical sample was prepared by dissolving 540 mg of the above product in 20 ml of methylene chloride and the solution was treated with activated charcoal and filtered. 50 ml of ethanol were added followed by concentration to 25 ml. After separating, 450 mg of product melting at 206° C., then 220° C. were obtained. The product was re-dissolved in 60 ml of ethanol at reflux, concentrated to 40 ml and separated after one night at ambient temperature to obtain 350 mg of the desired product melting at 210° C., then 220° C.

Analysis: C₁₆H₁₄BrNO₂S; molecular weight=364.28: Calculated: %C, 52.75; %H, 3.87; %Br, 21.94; %N, 3.85; %S, 8.80. Found: %C, 52.4; %H, 3.8; %Br, 22.0; %N, 3.9; %S, 8.8.

| NMR Spectrum (DMSO, 250 MHz) | | |
|---|---|---|
| S—C$\underline{H}$₂—CH | 2H | from 3.46 to 3.65 |
| H in ortho position of O—CH₃ | | 7.0 (d) |
| H in ortho position of Br | | 7.57 (d, j = 2H₃) |
| —OC$\underline{H}$₃ | | 3.81 |
| N—$\underline{H}$ | | 9.97 (s) |
| the other aromatics | | 7.60 (d,d) 1H |
| | | 7.44 (t) 1H |
| | | 7.14 to 7.32 (m) 3H |

STEP B: (±)-3-(3-bromo-4-methoxy phenyl)-2,3-dihydro-5-[2-(dimethylamino)-ethyl]-1,5-benzothiazepin-4(5H)-one hydrochloride 669 mg of dimethylamino ethanol in solution in 18.2 ml of tetrahydrofuran were added all at once to a solution of 1.82 g of the product of Step A in 18.2 ml of tetrahydrofuran and then 1.97 g of triphenyl phosphine were added. The mixture was ice-cooled, then a solution of 1.31 g of diethyl azodicarboxylate in 18.2 ml of tetrahydrofuran was added and the mixture was stirred for 19 hours at ambient temperature. The tetrahydrofuran was evaporated under reduced pressure, and extraction was done three times with 50 ml of N hydrochloric acid. The acid extracts were washed three times with 50 ml of ethyl acetate, the acid fraction was alkalinized with sodium hydroxide solution and extracted with methylene chloride. The extracts were washed with water and concentrated to dryness under reduced pressure to obtain 2 g of residue which was chromatographed on silica (eluant: methylene chloride-methanol 9-1) to obtain 1 g of the desired product in the form of a base.

Preparation of the hydrochloride

A solution of hydrochloric ethyl acetate in slight excess was added to a solution of 1 g of the base in 30 ml of ethyl acetate and 1 ml of acetone to obtain 1 g of the desired hydrochloride melting at 150° C. The hydrochloride was dissolved in 150 ml of acetone under reflux, followed by filtration and concentration to 20 ml to obtain 770 mg of product melting at 152° C. which was crystallized again by dissolving in 100 ml of acetone under reflux and adding 100 ml of ether at 25° C. to obtain 600 mg of the desired product melting at 152° C.

| NMR Spectrum (CDCl₃, 400 MHz) | | |
|---|---|---|
| 2.83 ppm (sl) | | the N—C$\underline{H}$₃'s |
| 3.12 (m) | 1H | } |
| 3.32 to 3.51 (m) | 3H | S—C$\underline{H}$₂—C$\underline{H}$ |
| 3.73 (d, d) | 1H | and |
| 4.18 (m) | 1H | N— |
| 4.65 (m) | 1H | C$\underline{H}$₂—C$\underline{H}$₂—N |
| 3.87 (s) | | |
| 6.85 (d) | | H in ortho position of OCH₃ |
| 7.23 (d, d) | | H in para position of Br |
| 7.47 (d) | | H in ortho position of Br |

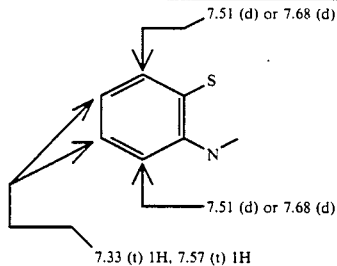

7.33 (t) 1H, 7.57 (t) 1H

EXAMPLE 3

2,3-dihydro-3-(4-methoxy phenyl)-5-[2-(4-morpholinyl)-ethyl]-1,5-benzothiazepine-4(5H)-one (Z)-2-butenedioate A solution of 1.3 g of diethyl azodicarboxylate in 20 ml of tetrahydrofuran was added at ambient temperature to a solution of 1.97 g of triphenyl phosphine in 50 ml of tetrahydrofuran and the mixture was stirred for 10 minutes. 1.43 g of the product of Step D of Example 1 were added, and then 1 g of morpholino ethanol was added. The mixture was stirred for 24 hours at ambient temperature and the tetrahydrofuran was evaporated off. The residue was taken up in 75 ml of ethyl acetate and extraction was done three times with 75 ml of N hydrochloric acid followed by washing twice with 75 ml of ethyl acetate and alkalization to pH 10 by adding sodium hydroxide solution. After extraction three times with 100 ml of ethyl acetate, the extracts were washed with water, dried and evaporated to dryness to obtain 1.7 g of product which was chromatographed on silica (eluant: ethyl acetate—triethylamine 95-5) to obtain 950 mg of product to which was was added 1.34 g of product obtained in the same way. The 2.29 g were chromatographed on silica (eluant: cyclohexane-dioxane 70-30) to obtain 1.6 g of the expected product in the form of a base.

Salification 1.6 g of the base were dissolved in 20 ml of isopropanol at 40° C. and to this solution was added a solution of 0.460 g of maleic acid in 20 ml of isopropanol. The mixture was left at rest for 16 hours and separated and washed with 5 ml of isopropanol and 10 ml of ethyl ether to obtain 1.2 g of the desired product melting at 176° C. By crystallization from acetonitrile, 780 mg of the product melting at 178° C. were obtained.

Analysis: $C_{26}H_{30}N_2O_7S$; molecular weight=514.58: Calculated: %C, 60.68; %H, 5.88; %N, 5.45; %S, 6.23. Found: %C, 60.4; %H, 5.9; %N, 5.5; %S, 6.1.

| NMR Spectrum (CDCl$_3$ 250 MHz) | |
|---|---|
| 3.78 (s) | O—C$\underline{H}_3$ |
| from 3.00 to 4.05 (m) | approx. 14H |
| 4.49 (m) | NCO—C$\underline{H}$—(C$_6$H$_5$) |
| 6.85 (d,j = 8.5) | 2H in ortho position of O—CH$_3$ |
| 7.21 (d,j = 8.5) | 2H in meta position of O—CH$_3$ |
| from 7.30 to 7.72 (m) | aromatic 4H's |
| 6.24 (S) | CO$_2$H—C$\underline{H}$=C$\underline{H}$—CO$_2$H |

EXAMPLE 4

2,3-dihydro-3-(4-methoxy phenyl)-5-[2-(1-piperidinyl)-ethyl]-1,5-benzothiazepin-4(5H)-one (E)-2-butenedioate Using the procedure of Example 3, 4.29 g of the product of Step D of Example 1 and 5.91 g of triphenyl phosphine were reacted together with 3.9 g of ethyl azodicarboxylate and 2.91 g of piperidinethanol. 5.91 g of dry extract was obtained which were chromatographed on silica (eluant: methylene chloride-methanol 95-5) to obtain 1.15 g of product which was crystallized from 3 ml of ethyl acetate to obtain 270 mg of the expected product in the form of a base melting at 110° C.

Salification 187 mg of fumaric acid in solution in 5 ml of methanol were added to a solution of 640 mg of the base product in 20 ml of isopropanol at 40° C. The mixture was concentrated to 3 ml and 5 ml of ethyl acetate were added. After separation, 770 mg of the expected product melting at 174° C. were obtained and a second purification was carried out by dissolving the above product in 5 ml of methanol at reflux. 30 ml of methyl ethyl ketone were added, followed by concentration to 5 ml. Separation was carried out after 20 hours at 0° C. to obtain 680 mg of the desired product.

Analysis: $C_{27}H_{32}N_2O_6S$; molecular weight =512.607: Calculated: %C, 63.26; %H, 6.29; %N, 5.46; %S, 6.25. Found: %C, 63.1; %H, 6.3; %N, 5.4; %S, 6.2.

| NMR Spectrum (CDCl$_3$ 250 MHz) | |
|---|---|
| 1.57 (m) for a<br>1.83 (m) for b and c | 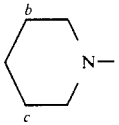 |
| from 3.0 to 3.5 (m) 8H | and 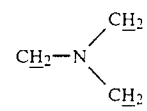 |
| | 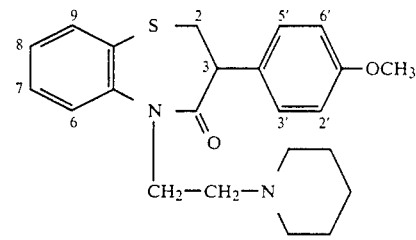 |
| 3.76 (dd, j = 12.5 and 6.5),<br>3.77 (s) | Hz<br>OC$\underline{H}_3$ |
| 4.06 (m)<br>4.42 (m) } | C$\underline{H}_2$—NCO |
| 6.84 (d, j = 8.5)<br>7.21 (d, j = 8.5)<br>7.27 (dl) | H$_2$' and H$_6$'<br>H$_3$' and H$_5$'<br>H$_9$ |
| 7.44 (tl)<br>7.49 (tl) } and | H$_7$<br>H$_8$ |
| 7.63 (dl)<br>6.72 (s)<br>9.67 (m) | H$_6$<br>C$\underline{H}$=C$\underline{H}$<br>mobile 2$\overline{H}$'s |

EXAMPLE 2

5-[2-(diethylamino)-ethyl]-2,3-dihydro-3-(4-methoxy phenyl)-1,5-benzothiazepin-4(5H)-one ethanedioate Using the procedure of Example 3, 2.86 g of the product of Step D of Example 1 and 3.94 g of triphenyl phosphine, 2.6 g of diethyl azodicarboxylate and 1.76 g of diethylaminoethanol were reacted and the 5 g of dry extract were chromatographed on silica (eluant: methylene chloride-methanol 95-5), to obtain 1.9 g of the desired product in the form of a base.

Salification 623 mg of oxalic acid in solution in 5 ml of methanol were added to a solution of 1.9 g of the base in 20 ml of hot isopropanol and the methanol was evaporated off. The mixture stood at rest for 3 hours, was separated and washed with 5 ml of isopropanol and 30 ml of ethyl ether to obtain 2.1 g of crude product melting at 195° C. 2.5 g of the product were crystallized from ethanol to obtain 2.2 g of the desired product melting 195° C.

Analysis: $C_{24}H_{30}N_2O_6S$; molecular weight=474.608: Calculated: %C, 60.74; %H, 6.37; %N, 5.90; %S, 6.75. Found: %C, 60.6; %H, 6.5; %N, 5.9; %S, 7.0.

| NMR Spectrum (250 MHz, DMSO) | |
|---|---|
| 2-N—CH$_2$—C$\underline{H}_3$ | 1.10 (t) |
| —N$^+$(C$\underline{H}_2$)$_3$ | from 2.85 to 3.32 (m) 6H |
| (C$_6$H$_6$)—S—C$\underline{H}_2$—C$\underline{H}$— | from 3.35 to 3.77 (m) |

-continued

| NMR Spectrum (250 MHz, DMSO) | |
|---|---|
| O—C$\underline{H}_3$ | 3.72 (s) |
| CO—N—C$\underline{H}_2$ | { 3.91 (m) <br> 4.17 (m) |
| H$_2'$ and H$_6'$ | 6.84 (d,j = 8.5) |
| H$_3'$ and H$_5'$ | 7.24 (d,j = 8.5) |
| other aromatics | { 7.37 (t) 1H <br> from 7.60 to 7.70 (m) 3H |

EXAMPLE 6

2,3-dihydro-5-[3-(dimethylamino)-propyl]-3-(4-methoxy phenyl)-1,5-benzothiazepin-4(5H)-one (E)-butenedioate 0.8 g of sodium hydride as a 50% dispersion in oil (the volume of hydrogen released was measured, = 110 ml) were added to a solution of 1.42 g of the product of Step D of Example 1 in 7 ml of dimethylformamide and 1.58 g of 3-(dimethylamino)-propane chloride hydrochloride were then added while cooling. The mixture was stirred for 4 hours at 60° C. and was then poured into 150 ml of water and extracted three times with 100 ml of ethyl acetate. The organic phase was washed with water, dried and evaporated to dryness to obtain 2.3 g of oil which was chromatographed on silica (eluant: ethyl acetate-methanol-triethylamine 60-40-3) to obtain 988 mg of desired product in the form of a base.

Salification 830 mg of the product were dissolved in 10 ml of isopropanol and added to a solution of 260 mg of fumaric acid in 10 ml of boiling methanol. The mixture was stirred and then left at rest for 3 hours at ambient temperature. Separation was carried out to obtain 860 mg of crude product melting at 182° C. which was crystallized from 35 ml of ethanol at reflux to obtain 740 mg of the desired product melting at 184° C.

Analysis: $C_{25}H_{30}N_2O_6S$; molecular weight = 486.583: Calculated: %C, 61.71; %H, 6.21; %N, 5.76; %S, 6.59. Found: %C, 61.7; %H, 6.4; %N, 5.7; %S, 6.4.

| NMR Spectrum (250 MHz, DMSO) | |
|---|---|
| 1.66 (m) | central CH$_2$ |
| 2.26 (s) | NH$_3$'s |
| 3.71 (s) | $-\overset{\parallel}{C}-O-C\underline{H}_3$ |
| 4.13 (m) | CH$_2$—C$\underline{H}$=CH$_2$ (R$_6$H$_5$) |
| from 3.3 to 3.8 | the other CH$_2$'s |
| 6.54 (s) | the ethylenics |
| 6.81 (d, j=8.5 Hz) | aromatics in ortho position of OCH$_3$ |
| 7.22 (d, j=8.5 Hz) | aromatics in meta position of OCH$_3$ |
| 7.33 (t) | H$_7$ or H$_8$ |
| 7.67 (d) | H$_6$ or H$_9$ |
| 7.59 (m) | 2H |

EXAMPLE 7

2,3-dihydro-3-(4-methoxy phenyl)-5-[2-(4-methyl-1-piperazinyl)-ethyl]-1,5-benzothiazepin-4(5H)-one dichlorhydrate Using the procedure of Example 3, 2.86 g of the product of Step D of Example 1, 3.94 g of triphenyl phosphine, 2.6 g of diethyl azodicarboxylate and 1.76 g of 1-[(2-hydroxy)-ethyl]-4-methyl piperazine were reacted to obtain after chromatography on silica (eluant: methylene chloride-methanol 94-6), 1.32 g of the expected product in the form of a base.

Salification 15 ml of a solution of 3.6N hydrochloric acid in ethyl acetate were added to a solution of 1.3 g of the base in 10 ml of isopropanol and the mixture stood at rest for 4 hours at ambient temperature. After separation, 1.10 g of the desired product melting at 205° C. were obtained which was crystallized from an ethyl ether-methanol mixture (1-1) to obtain 800 mg of the desired product melting at 205° C.

Analysis: $C_{23}H_{31}Cl_2N_3O_2S$; molecular weight = 484.492: Calculated: %C, 57.02; %H, 6.45; %Cl, 14.63; %N, 8.67; %S, 6.62. Found: %C, 57.0; %H, 6.6; %Cl, 14.5; %N, 8.5; %S, 6.6.

| NMR Spectrum (300 MHz, DMSO) | |
|---|---|
| 2.79 (s) | N—C$\underline{H}_3$ |
| 3.72 (s) | O—C$\underline{H}_3$ |
| 4.04 (m) <br> 4.27 (m) | CO—N—C$\underline{H}_2$ |
| 6.84 (d) | H$_2'$ and H$_6'$ |
| 7.24 (d) | H$_3'$ and H$_5'$ |
| 7.38 (dt) <br> 7.61 (dt) <br> 7.68 (dt) | aromatic 4H's |
| 11.86 (ep) < mobile 2H's | |
| from 3.0 to 3.8 (m) | the other protons. |

EXAMPLE 8

(±)-2,3-dihydro-3-(4-methoxy phenyl)-5-[2-[4-(2-methoxy phenyl)-1-piperazinyl]-ethyl]-1,5-benzothiazepin-4(5H)-one ethanedioate Using the procedure of Example 3, 2.85 g of product of Step D of Example 1, 3.15 g of triphenyl phosphine, 2.09 g of diethyl azodicarboxylate and 2.84 g of 4-(2-methoxy phenyl)-1-piperazine ethanol were reacted to obtain after chromatography on silica (eluant: cyclohexane-dioxane 7-3), 1.23 g of the expected product in the form of a base.

Salification 570 mg of the product were dissolved in 30 ml of isopropanol and 143 mg of oxalic acid in solution in 1 ml of methanol were added. The mixture was concentrated to 15 ml in total and after separating, 419 mg of expected product were obtained melting at 128° C. which was crystallized from 50 ml of ethanol, then concentrated to 20 ml in total to obtain 260 mg of the expected product melting at 130° C.

EXAMPLE 9

(±)-5-[2-[[bis(1-methyl ethyl)]-amino]-ethyl]-2,3-dihydro-3-(4-methoxy phenyl)-1,5-benzothiazepin-4(5H)-one hydrochloride Using the procedure of Example 3, 2 g of the product of Step D of Example 1, 2.2 g of triphenyl phosphine, 1.22 g of diisopropylamino ethanol and 1.46 g of diethyl azodicarboxylate were reacted to obtain after chromatography on silica (eluant: methylene chloride-methanol 95-5), 1.76 g of the expected product in the form of a base.

Salification

A solution of hydrochloric acid in ethyl acetate was added to a solution of 1.76 g of base in 5 ml of ethyl acetate until a pH of 2 was reacted to obtain 1.28 g of crude product melting at 142° C. which was crystallized twice from an ethanol-ether mixture to obtain 600 mg of the expected product melting at 160° C.

Analysis: $C_{24}H_{33}ClN_2O_2S$; molecular weight=449.06 (Product solvated at 3.8%): Calculated: %C, 64.19; %H, 7.41; %Cl, 7.89; %N, 6.24; %S, 7.14. Found: %C, 64.5; %H, 7.6; %Cl, 7.7; %N, 6.1; %S, 6.9.

EXAMPLE 10

(±)-2,3-dihydro-3-(3,4-dimethoxy phenyl)-5-[2-(dimethylamino)-ethyl]-1,5-benzothiazepin-4(5H)-one hydrochloride Using the procedure of Example 3, 3.15 g of the product of Step D of preparation A, 3.15 g of triphenyl phosphine, 1.2 ml of N,N-dimethyl ethanol amine and 1.9 ml of diethyl azodicarboxylate were reacted to obtain 2.1 g of the expected product in the form of a base.

Salification

Hydrochloric ethanol was added to a solution of 2.1 g of the base in 9 ml of isopropanol until a pH of 1 was reacted to obtain 1.2 g of the desired product melting at 148° C. 1.2 g were crystallized from 8 ml of isopropanol to obtain 800 mg of the product melting at 150° C.

| NMR Spectrum (CDCl₃, 250 MHz) | | |
|---|---|---|
| 3.47 (m) | 2H | S—CH₂—CH |
| 3.74 (dd) | 1H | S—CH₂—CH |
| 3.85 (s) and 3.87 (s) | | the OCH₃'s |
| 3.12 and 3.47 (m) | 2H | 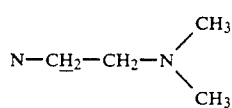 |
| 4.19 and 4.57 (m) | 2H | 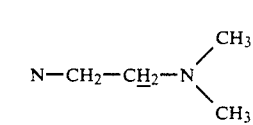 |
| 2.78 and 2.88 (resolved s) | | 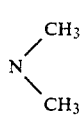 |
| 7.33–7.54–7.68 | 4H | the aromatics |
| 6.83 (m) | 3H | other aromatics of the trisubstituted phenyl |
| 12.62 | | mobile H |

PREPARATION A 2,3-dihydro-3-(3,4-dimethoxy phenyl)-1,5-benzothiazepin-4(5H)-one

STEP A: Ethyl 3,4-dimethoxy-α-methylene benzeneacetate 28.7 g of diethyl oxalate were added to a 0.1 mole suspension of sodium ethylate prepared from 2.29 g of sodium in 60 ml of toluene dried on siliporite and then 20 g of ethyl 3,4-dimethoxy-phenylacetate were added at 30° C. to 40° C. The resultant mixture was maintained for 2 hours at reflux, then cooled at −30° C. and 24.6 ml of 4N sulfuric acid were added rapidly. The mixture was left to return to −10° C. and a few mg of hydroquinone were added, then 8 ml of formaldehyde at 36% in an aqueous solution (stabilized with 10% of methanol) were added. Then at −10° C., a saturated solution of potassium carbonate was added slowly and the medium was left to return to ambient temperature. The mixture was stirred for 2 hours and 4 ml of 36% formaldehyde were added. The mixture was stirred for 16 hours at ambient temperature and 180 ml of water were added, followed by decanting and concentrating to dryness under reduced pressure to obtain 21 g of the expected product which was used as is for the following step.

STEP B: 3,4-dimethoxy-α-methylene benzeneacetic acid

Using the procedure of Step E of Example 1, 18 g of the product of Step A were reacted to obtain 8.8 g of the desired product melting at 128° C. which was used as is for the following step. 540 mg of product were crystallized from 15 ml of isopropyl ether to obtain 300 mg of desired product melting at 132° C.

| NMR Spectrum (CDCl₃, 250 MHz) | |
|---|---|
| 3.90 (s) | the CH₃—O's |
| 6.86 (d, j=8) | 1H |
| 7.00 (d, j=2) | 1H |
| 7.03 (dd, j=8 and 2) | 1H |
| 5.99 (d, j=1) | —C—COOH |
| 6.49 (d, j=1) | ‖ CH₂ |
| 11.56 | COOH |

STEP C: α-[(2-amino phenyl thio)-methyl]-3,4-dimethoxy benzeneacetic acid

Using the procedure of Step F of Example 1, 7.8 g of the product of Step B were reacted to obtain 9.1 g of the desired product melting at 162° C. which was used as is for the following step. 1 g of product was crystallized from 15 ml of acetonitrile to obtain 650 mg of an analytical sample melting at 164° C.

Analysis: $C_{17}H_{19}NO_4S$; molecular weight=333.33: Calculated: %C, 61.24; %H, 5.74; %N, 4.20; %S, 9.61. Found: %C, 61.1; %H, 5.9; %N, 4.4; %S, 9.7.

| NMR Spectrum: (DMSO, 250 MHz) | |
|---|---|
| S—CH₂—C | 2.97 (dd, j=6 and 13) |
| | 3.33 (dd, j=9 and 13) |

-continued

NMR Spectrum: (DMSO, 250 MHz)

3.56 (dd, j=6 and 9) $-C\underline{H}-\phi$

| | |
|---|---|
| 6.59 (t) (1H) | |
| 7.08 (t) (1H) | the aromatics |
| 7.28 (d) (1H) | |
| 6.80 (m) (4H) | |

STEP D: 2,3-dihydro-3-(3,4-dimethoxy phenyl)-1,5-benzothiazepin-4(5H)-one

A solution of 9.1 g of the product of Step C, 180 ml of methylene chloride, 6.25 g of 1-ethyl-3-(3-dimethylamino propyl) carbodiimide hydrochloride and 9 ml of triethylamine was stirred for 90 minutes at ambient temperature and the methylene chloride was evaporated off. The residue was taken up in 90 ml of ethyl acetate and after separation, 7.8 g of the expected product were obtained melting at 174° C. An analytical sample was obtained by crystallization of 200 mg of crude product from 10 ml of ethyl acetate to obtain 120 mg of the desired product melting at 184° C.

Analysis: $C_{17}H_{17}NO_3S$; molecular weight=315.38: Calculated: %C, 64.73; %H, 5.43; %N, 4.44; %S, 10.16. Found: %C, 64.8; %H, 5.4; %N, 4.5; %S, 10.3.

NMR Spectrum (CDCl₃, 250 MHz)

| | |
|---|---|
| 3.85 (s) | the O—C$\underline{H}_3$'s |
| 3.86 (s) | |
| 3.85 | H$\underline{C}$— (aromatic) |
| 6.82 (m) 2H | |
| 6.89 (s) 1H | |
| 3.46 to 3.66 | S—C$\underline{H}_2$— |
| 7.16 (dd) | |
| 7.23 (td) | the aromatics |
| 7.40 (td) | |
| 7.66 (dd) | |
| 7.89 | N$\underline{H}$ |

EXAMPLE 11
3-(4-chloro-phenyl)-2,3-dihydro-5-[2-(dimethylamino)-ethyl]-1,5-benzothiazepin-4(5H)-one hydrochloride Using the procedure of Example 3, 3.5 g of the product of Step D of preparation B, 1.8 ml of N-dimethyl ethanol amine, 4.72 g of triphenyl phosphine and 2.83 ml of diethyl azodicarboxylate were reacted to obtain 3 g of the expected product melting at 148° C., in the form of a base.

Salification

The 3 g of base were suspended in 30 ml of isopropanol and a solution of hydrochloric acid in ethanol was added until a pH of 1 was obtained. Separation was carried out, then washing with isopropanol to obtain 2.7 g of the desired product melting at 248° C.

Analysis: $C_{19}H_{21}ClN_2SO$, HCl; molecular weight=397.36: Calculated: %C, 57.42; %H, 5.58; %Cl, 17.84; %N, 7.05; %S, 8.07. Found: %C, 57.4; %H, 5.6; %Cl, 17.9; %N, 7.0; %S, 7.8.

NMR Spectrum (DMSO. 250 MHz)

| | |
|---|---|
| $N(C\underline{H}_3)(C\underline{H}_3)$ | 2.75 |
| $\underset{/}{\overset{\backslash}{C}}-N-CO$ | approx. 4.01 (m) (1H) |
| $C\underline{H}_2$ | and 4.27 (m) (1H) |
| S—C$\underline{H}_2$—CH and $\underset{/}{\overset{\backslash}{N}}$—C$\underline{H}_2$—CH$_2$ | approx. 3.06 (m) (1H) 3.34 (m) (1H) 3.30 (m) (2H) |
| N—CO—C$\underline{H}$—CH$_2$ $\mid$ $\phi$ | 3.81 |
| aromatics | from 7.30 to 7.50 (5H) from 7.55 to 7.8 (3H) |

IR Spectrum (CHCl₃ on Nicolet)

| Absence NH type lactame | Presence of NH⁺ |
|---|---|
| C=O | 1669 cm⁻¹ |
| aromatics | 1594 cm⁻¹ |
| | 1581 cm⁻¹ |
| | 1568 cm⁻¹ |
| | 1494 cm⁻¹ |

PREPARATION B
2,3-dihydro-3-(4-chloro phenyl)-1,5-benzothiazepine-4(5H)-one

STEP A: Methyl 4-chloro-α-methylene benzeneacetate

A solution of 51 g of methyl 4-chlorophenyl-acetate, 44 g of dimethyl oxalate and 320 ml of ether was added to a suspension of 0.351 mole of sodium methylate (prepared from 8.06 g of sodium) in 510 ml of ether and the mixture was stirred for 17 hours at reflux. 250 ml of ether were added and cooled and 250 ml of 2N hydrochloric acid were added slowly until a pH of 1 was obtained. After decanting, washing with 50 ml of 2N hydrochloric acid, then with water saturated with sodium chloride, and evaporating to dryness, 69 g of oily product were obtained which were suspended in 500 ml of water in the presence of trace amounts of hydroquinone 50 ml of 40% formaldehyde were added and the mixture was stirred for 3 hours at ambient temperature. Extraction was done with ethyl acetate and the extracts were washed with water, dried and evaporated to dryness. The 55 g of residue were chromatographed on silica (eluant: cyclohexane-ethyl acetate 95-5) to obtain 33 g of the desired product which is used as is for the following step.

STEP B: 4-chloro-α-methylene benzeneacetic acid 530 ml of a 0.33M solution of potassium hydroxide were added to a solution of 700 ml of tetrahydrofuran and 15 g of the product of Step A and the mixture was stirred for 76 hours at ambient temperature. The tetrahydrofuran was evaporated off acidification was effected with 2N hydrochloric acid. After separating, washing with water and drying, 11.75 g of the expected product were obtained melting at 110° C., which was used as is for the following step. An analytical sample was prepared by crystallization of 350 mg of product from 50 ml of water to obtain 200 mg of the product melting at 110° C.

Analysis: $C_9H_7ClO_2$; molecular weight=182.6: Calculated: %C, 59.19; %H, 3.86; %N, 19.41. Found: %C, 59.1; %H, 3.8; %N, 19.5.

STEP C: α-[[(2-amino phenyl)-thio]-methyl]-4-chlorobenzeneacetate acid

A solution of 6 g of the acid of Step B in 90 ml of ethanol with 3.5 ml of 2-aminothiophenol was stirred for 17 hours at reflux and the mixture was evaporated to dryness. The residue was taken up in 50 ml of methylene chloride with 5% methanol and after separation, 6 g of the desired product were obtained melting at 142° C. which was used as is for the following step. An analytical sample was prepared by crystallization of 350 mg of product from 20 ml of cyclohexane and 2 ml of isopropanol to obtain 220 mg of product melting at 142° C.

Analysis: $C_{15}H_{14}ClNO_2S$; molecular weight=307.789: Calculated: %C, 58.53; %H, 4.58; %Cl, 11.52; %N, 4.55; %S, 10.41. Found: %C, 58.5; %H, 4.5; %Cl, 11.7; %N, 4.5; %S, 10.2.

STEP D: 2,3-dihydro-3-(4-chloro phenyl)-1,5-benzothiazepin-4(5H)-one

A solution of 5 g of the acid of Step C, 125 ml of methylene chloride and 3.73 g of 1-ethyl-3-(3-dimethylamino-propyl)carbodiimide hydrochloride was stirred for 2 hours 30 minutes at ambient temperature and the solution was evaporated to dryness. The residue was taken up in 25 ml of ethanol and separation was carried out, followed by washing with ethanol to obtain 3 g of the desired product melting at 180° C. By chromatography of the filtrate on silica (eluant: ethyl acetate), a second amount of 500 mg melting at 180° C. was obtained after crystallization from 10 ml of ethanol. The product was used as is for the following step. An analytical sample was prepared by crystallization of 350 mg of product from 10 ml of ethanol to obtain 230 mg of product melting at 180° C.

Analysis: $C_{15}H_{12}ClNSO$; molecular weight=289.77: Calculated: %C, 62.17; %H, 4.17; %N, 4.83; %Cl, 12.23; %S, 11.06. Found: %C, 62.3; %H, 4.2; %N, 4.9; %Cl, 12.3; %S, 10.74.

EXAMPLE 12

2,3-dihydro-5-[2-(dimethylamino)-ethyl]-3-(2-methoxy-phenyl)-1,5-benzothiazepin-4(5H)-one hydrochloride Using the procedure of Example 3, 2.85 g of the product of Step E of preparation C, 1.5 ml of N-dimethyl ethanol amine, 3.93 g of triphenyl phosphine and 2.36 ml of diethyl azodicarboxylate were reacted to obtain after chromatography on silica (eluant: methylene chloride-methanol 90-10), 1.6 g of the desired product in the form of a base.

Salification 900 mg of the base were dissolved in 5 ml of isopropanol and hydrochloric ethanol was added until a pH of 1 was obtained. Separation was carried out, followed by washing with isopropanol and drying to obtain 800 mg of the desired product melting at approx. 195° C. After a crystallization of 800 mg from 5 ml of isopropanol, 630 mg were collected melting at 195° C.

Analysis: $C_{20}H_{24}N_2O_2S$, HCl; molecular weight=392.94: Calculated: %C, 61.13; %H, 6.41; %N, 7.13; %Cl, 9.02; %S, 8.16. Found: %C, 60.8; %H, 6.5; %N, 7.0; %Cl, 9.3; %S, 7.9.

Lost under vacuum at 100° C., 2.6%.

| NMR Spectrum: ($CDCl_3$, 250 MHz) | | |
|---|---|---|
| $-CH_2-CH_2-N\begin{array}{c}CH_3\\ \diagdown\\ CH_3\end{array}$ | 4.20 (m)–4.59 (m) | |
| $CH_2-CH_2-N\begin{array}{c}CH_3\\ \diagdown\\ CH_3\end{array}$ | 3.12 (m)–3.41 (m) | |
| $-N\begin{array}{c}CH_3\\ \diagdown\\ CH_3\end{array}$ | 2.81 | |
| $O-CH_3$ | 3.70 | |
| $S-CH_2-\underline{CH}-CO$ <br> $\vert$ <br> $(C_6H_5)$ | 4.20 (t, j=10 Hz) | |
| $S-\underline{CH_2}-CH-CO$ <br> $\vert$ <br> $(C_6H_5)$ | 3.53 (d) | |
| 1H in ortho position of $OCH_3$ | 6.80 (d) | 1H |
| the aromatics | 6.97 (t) | 1H |
| | 7.2 to 7.35 | 3H |
| | 7.53 (m) | 2H |
| | 7.67 (d, d) | 1H |

PREPARATION C

2,3-dihydro-3-(2-methoxy phenyl)-1,5-benzothiazepin-4(5H)-one

STEP A: Methyl 2-methoxy-phenyl-acetate

A solution of 40 g of 2-methoxy-phenyl-acetic, 160 ml of methanol and 8 ml of an aqueous solution of sulfuric acid (at 5% by volume) was stirred for 52 hours at ambient temperature and then was concentrated to approx. 100 ml in total, and then 400 ml of water were added. Extraction was done with methylene chloride and the organic phase was washed with a normal solution of potassium carbonate and with water. After evaporation to dryness under reduced pressure, 41 g of product were obtained which was used as is for the following step.

STEP B: Methyl 2-methoxy-α-methylene-benzeneacetate

A solution of 40 g of the product of Step A and 35 g of dimethyl oxalate in 250 ml of ether was added to a 0.280 mole suspension of sodium methylate (prepared from 6.4 g of sodium) in 400 ml of ether. This mixture was stirred for 17 hours at reflux, cooled, and 250 ml of ether were added. Then, 200 ml of 2N hydrochloric acid were added until a pH of 1 was obtained. Decanting was done followed by washing with 2N hydrochloric acid, then with a saturated solution of sodium chloride. After evaporation to dryness, 51 g of an oil were obtained which were suspended in 400 ml of water in the presence of trace amounts of hydroquinone. 40 ml of 40% formaldehyde and 33.4 g of potassium carbonate were added and the mixture was stirred for 3 hours at ambient temperature. After extraction with ethyl acetate, the organic phase was washed with water, dried and evaporated off. The residue was chromatographed on silica (eluant: cyclohexane ethyl acetate 95-5) to obtain 24 g of the desired product which was used as is for the following step.

STEP C: 2-methoxy-α-methylene-benzeneacetic acid 765 ml of an aqueous solution (0.33M) of potassium hydroxide were added to a solution of 21 g of the product of Step B in 1 liter of tetrahydrofuran and the mixture was stirred for 48 hours at ambient temperature. The tetrahydrofuran was evaporated off and the aqueous phase was cooled and acidified with 2N hydrochloric acid. Separation was carried out, then washing with water and drying to obtain 16.8 g of the product which was used as is for the following step. An analytical sample was prepared by hot and cold crystallization of 1.6 g of product from 30 ml of isopropyl ether to obtain 0.8 g of the product melting at 146° C.

Analysis: $C_{10}H_{10}O_3$; molecular weight=178.18: Calculated: %C, 67.40; %H, 5.65. Found: %C, 67.4; %H, 5.8.

STEP D: α-[[(2-amino phenyl)-thio]-methyl]-2-methoxy-benzeneacetic acid

A solution of 230 ml of ethanol, 16.3 g of the product of Step C and 9.8 ml of 2-aminothio-phenol was refluxed for 4 hours and the ethanol was evaporated off. The 28 g of residue were chromatographed on silica (eluant: cyclohexane-ethyl acetate (6-4)) to obtain 14 g of product which was crystallized from 25 ml of cyclohexane and 1 ml of isopropanol to obtain 12.5 g of the desired product melting at 85° C. which was used as is for the following step. An analytical sample was prepared by crystallization of 180 mg of the product from 3 ml of cyclohexane and 0.1 ml of isopropanol to obtain 80 mg of purified product melting at 90° C.

Analysis: $C_{16}H_{17}NO_3S$; molecular weight=303.372: Calculated: %C, 63.34; %H, 5.65; %N, 4.61; %S, 10.57. Found: %C, 63.5; %H, 5.8; %N, 4.6; %S, 10.5.

| NMR Spectrum (CDCl₃, 60 MHz) | |
|---|---|
| 169 to 213.5 | S—C$\underline{H}_2$—CH |
| 241 to 256 | S—C$\overline{H}_2$—C$\underline{H}$ |
| 220.5 | O—CH₃ |
| 309 | { H of the COO$\underline{H}$ <br> H of the N$\underline{H}_2$ |
| 388 to 444 | the aromatics |

STEP E: 2,3-dihydro-3-(2-methoxy phenyl)-1,5-benzothiazepin-4(5H)-one 11.7 g of the acid of Step D, 7.95 g of dicyclohexylcarbodiimide and 350 ml of ethanol were stirred for 6 hours at ambient temperature and after evaporation to dryness, the residue was taken up in 1500 ml of methylene chloride. The insoluble part was filtered off and the filtrate was concentrated to dryness. The residue was taken up in 1500 ml of ethanol and separation was effected to obtain 9.6 g of the desired product melting at 219° C. which was used as is for the following step. An analytical sample was prepared by crystallizing 350 mg of product from 40 ml of ethanol to obtain 240 mg of the desired structure melting at 223° C.

Analysis: $C_{16}H_{15}NO_2S$; molecular weight=285.35: Calculated: %C, 67.34; %H, 5.30; %N, 4.91; %S, 11.23. Found: %C, 67.2; %H, 5.2; %N, 4.9; %S, 11.3.

| NMR Spectrum (DMSO, 250 MHz) | |
|---|---|
| S—C$\underline{H}_2$—CH—CO <br> \| <br> (C₆H₅) | 3.50 to 3.72 |
| S—CH₂—C$\underline{H}$—CO <br> \| <br> (C₆H₅) | 4.13 |
| O—C$\underline{H}_3$ | 3.63 |
| aromatics | 6.84 to 7.61 |

EXAMPLE 13

2,3-dihydro-5-8 2-(dimethylamino)-ethyl]-3-(4-methoxy phenyl)-1,5-benzothiazepin-4(5H)-one (E)-2-butenedioate Using the procedure of Example 3, 3 g of the product of Step D of Example 1, 4.11 g of triphenyl phosphine, 1.58 ml of N-dimethyl ethanol amine and 2.47 g of diethyl azodicarboxylate were reacted to obtain after chromatography on silica (eluant: methylene chloride-methanol 95-5), 2.8 g of the desired product in the form of a base.

Salification 2.8 g of the product were dissolved in 30 ml of ethyl acetate and a solution of 0.91 g of fumaric acid in 25 ml of ethanol were added. After separation, 1.8 g of the desired product melting at 162° C. were obtained. The product was crystallized from 225 ml of ethyl acetate, and concentrated to 100 ml to obtain 1.5 g of product melting at 162° C.

Analysis: $C_{24}H_{28}N_2O_6S$; molecular weight=472.54: Calculated: %C, 60.99; %H, 5.97; %N, 5.92; %S, 6.78. Found: %C, 61.0; %H, 6.0; %N, 5.9; %S, 6.6.

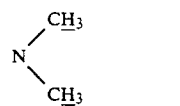

EXAMPLE 14

(±)-2,3-dihydro-5[2-(dimethylamino)-ethyl]-3-(4-methoxy phenyl)-1,5-benzothioazepin-4(5H)-one (E) 2-butenedioate STEP A: Ethyl (+)-2,3-dihydro-3-(4-methoxy phenyl)-4-oxo-1,5-benzothiazepin-5(4H)-acetate 1.35 g of sodium hydride in a 50% dispersion in oil were added at between +15° and +20° C. to a solution of 6.84 g of the product of Step D of Example 1 in 30 ml of dimethylformamide and the mixture was stirred for 15 minutes at 20° C. (volume of hydrogen released: 540 ml) and was cooled to +5° C. to +10° C. 3.12 ml of ethyl bromoacetate were added and the mixture was stirred for one hour at ambient temperature. The mixture was poured into 200 ml of water and was extracted with ether. The extracts were washed with water and after evaporation under reduced pressure, 9 g of an oil were obtained which was chromatographed on silica (eluant: methylene chloride-methanol 99-1) to obtain 6.8 g of the expected product which was used as is for Step B.

STEP B: (±)-2,3-dihydro-3-(4-methoxy phenyl)-4-oxo-1,5-benzothiazepin-5(4H)-acetic acid 6.8 g of the product of Step A were dissolved in 136 ml of a mixture of equal parts of water, of acetic acid and sulfuric acid and the mixture was stirred for 19 hours at ambient temperature. 400 ml of water were added slowly with stirring for 10 minutes, and separation was effected to obtain 5.3 g of the expected product melting at 180° C. which was used as is for following step. An analytical sample was prepared by two successive crystallizations from 20 volumes of ether at reflux starting with 2.7 g of the acid to obtain 1.15 g of the product melting at 190° C. (approx.).

Analysis: $C_{18}H_{17}NO_4S$; molecular weight = 343.40: Calculated: %C, 62.96; %H, 4.99; %N, 4.08, %S, 9.33. Found: %C, 62.9; %H, 5.0; %N, 3.9; %S, 9.3.

STEP C: 2,3-dihydro-5-(2-hydroxy ethyl)-3-(4-methoxy phenyl)-1,5-benzothiazepine-4-(5H)-one 7.5 ml of 2M borane-dimethyl sulfide complex in tetrahydrofuran were added at +10° C. over 10 minutes to a solution of 3.44 g of the acid of Step B in 34.4 ml of tetrahydrofuran and after 18 hours of stirring at ambient temperature, a further 1 ml of the solution of borane-dimethyl sulfide was added with further stirring for 6 hours at ambient temperature. 5 ml of methanol were added, followed by evaporation to dryness under reduced pressure. 100 ml of water were added and extraction was done three times with 40 ml of methylene chloride, followed by filtering, drying and evaporation to dryness under reduced pressure. The 3.8 g of residue were crystallized from 5 ml of ether to obtain 1.9 g of the expected product melting at 133° C. which was used as is for the following step. An analytical sample was prepared by crystallization of 150 mg of the product from ether to obtain 125 mg of the desired product melting at 135° C.

Analysis: $C_{18}H_{19}NO_3S$; molecular weight = 329.40: Calculated: %C, 65.63; %H, 5.81; %N, 4.25; %S, 9.73. Found: %C, 65.5; %H, 5.8; %N, 4.1; %S, 9.7.

STEP D: 2,3-dihydro-5-(2-chloro ethyl)-3-(4-methoxy phenyl)-1,5-benzothiazepin-4(5H)-one 0.14 ml of thionyl chloride was added to a solution of 329 mg of the product of Step C in 3.3 ml of methylene chloride and the mixture was stirred for 15 minutes at ambient temperature, then evaporated to dryness under reduced pressure. The residue was taken up in 25 ml of ether at reflux, treated with activated charcoal, filtered and concentrated to 7 ml. After separation, 300 mg of the expected product melting at approx. 70° C. were obtained which was used as is for Step E. An analytical sample was prepared by dissolving 300 mg of the product in 10 ml of hot methyl ethyl ketone which was concentrated to 2 ml, then adding 2 ml of pentane. After separating, 65 mg of the desired product melting at approx. 70° C. were obtained.

Analysis: $C_{18}H_{18}NO_2ClS$; molecular weight = 347.85 + ½ mole of methyl ethyl ketone: Calculated: %C, 62.57; %H, 5.78; %N, 3.65; %Cl, 9.23. Found: %C, 62.5; %H, 5.8; %N, 3.7; %Cl, 9.3.

STEP E:
(±)-2,3-dihydro-5-[2-(dimethylamino)-ethyl]-3-(4-methoxy phenyl)-1,5-benzothiazepin-4(5H)-one (E)-2-butenedioate A suspension of 348 mg of the product of Step D in 1.7 ml of 33% dimethylamine in ethanol was stirred for 30 minutes at ambient temperature in an enclosed apparatus, and for 18 hours at 50° C. The mixture was evaporated to dryness under reduced pressure and after 40 ml of a saturated solution of sodium bicarbonate were added, extraction was done with methylene chloride. The extracts were washed with water, dried and evaporated to dryness under reduced pressure. The 280 mg of residue were chromatographed on silica (eluant: methylene chloride-methanol 95-5) to obtain 43 mg of the expected product in the form of a base.

Salification 14 mg of fumaric acid and 15 ml of ethyl acetate were added to a solution of 43 mg of the base in 3 ml of methanol and the resultant mixture was concentrated to 4 ml, separated, washed with ethyl acetate and then with ether to obtain 40 mg of the desired product melting at 162° C.

EXAMPLE 15

(±)-2,3-dihydro-5-[2-dimethylamino)-ethyl]-3-(4-hydroxy phenyl)-1,5-benzothiazepin-4(5H)-one hydrochloride 2.1 g of the product of Example 13 were treated with 20 ml of concentrated hydrobromic acid at ambient temperature for 24 hours and the reaction medium was poured over 100 g of water and ice. Then, the medium was neutralized by the addition of sodium bicarbonate and extracted with methylene chloride. The extracts were washed twice with 20 ml of water, dried and evaporated to dryness under reduced pressure to obtain 1.54 g of the expected product in the form of a base.

Salification

A solution of hydrochloric acid in ethyl acetate was added to a solution of 1.5 g of the product in 10 ml of methyl ethyl ketone until a pH of 1 was obtained. The ethyl acetate was evaporated while maintaining a constant volume by the addition of methyl ethyl ketone. Separation was effected, followed by washing with methyl ethyl ketone, then with ethyl ether to obtain 740 mg of the desired product melting at approximately 220° C. An analytical sample was prepared from 1.22 g of product crystallized from 40 ml of isopropanol to obtain 900 mg of pure product melting at 240° C.

Analysis: $C_{19}H_{23}ClN_2O_2S$; molecular weight=378.924: Calculated: %C, 60.23; %H, 6.12; %N, 9.36; %Cl, 7.39; %S, 8.46. Found: %C, 60.1; %H, 6.2; %N, 9.4; %Cl, 7.3; %S, 8.4.

| NMR Spectrum (DMSO, 250 MHz): | |
|---|---|
| $\diagup$CH$_3$ N$\diagdown$ $\diagdown$CH$_3$ | 2.75 (s) |
| the 3 CH$_2$'s and N —CHC=O $\mid$ (C$_6$H$_5$) | 3.03 (m) 1H<br>3.30 to 3.50 (m) 3H<br>3.62 (m) 1H<br>3.99 (m) 1H<br>4.27 (m) 1H |
| mobile 2H's | 9.41 (s) 1H<br>10.68 (sl) 1H |
| the aromatics | from 7.09 to 7.67 |

EXAMPLE 16

(±)-N-(2-diethylamino-ethyl)-2,3-dihydro-3-(4-methoxy phenyl)-4-oxo-1,5-benzothiazepin-5(4H)-acetamide hydrochloride 1.71 g of (±) 2,3-dihydro-3-(4-methoxyphenyl)-4-oxo-1,5-benzothiazepin-5-(4H)-acetic acid of Step B of Example 14, 17 ml of methylene chloride, 1.74 g of N,N-diethylethylene diamine and 3.82 g of 1-ethyl-3-(dimethylaminopropyl)-carbodiimide hydrochloride were stirred for 90 minutes and the solution was poured over 50 ml of water. 10 ml of a saturated aqueous solution of sodium bicarbonate were added, and extraction was done with methylene chloride. The extracts were washed with water, dried and the solvent was eliminated under reduced pressure to obtain 3.6 g of crude product which was chromatographed on silica (eluant: methylene chloride-methanol 8-2) to obtain 1.6 g of the expected product in the form of a base. The base was dissolved in 5 ml of isopropanol and a solution of hydrochloric acid in ethyl acetate was added to obtain 1.5 g of the expected hydrochloride which was crystallized from isopropanol to obtain 525 mg of pure product melting at 160° C.

Analysis: $C_{24}H_{31}N_3O_3S$, HCl: Calculated: %C, 60.30; %H, 6.75; %Cl, 7.42; %N, 8.79; %S, 6.71. Found: %C, 60.0; %H, 6.7; %Cl, 7.2; %N, 8.8; %S, 6.7.

| NMR Spectrum (DMSO, 250 MHz) | |
|---|---|
| 1.19 (t)<br>1.28 (t) | CH$_3$—CH$_2$ |
| 3.76 (s) | OCH$_3$ |
| 4.25 (d, J=17 Hz)<br>4.58 (d, J=17 Hz) | N—CH$_2$—C$\parallel$O |
| 6.82 (d) | 2H in ortho position of OCH$_3$ |
| 7.31 (d) | 2H in meta position of OCH$_3$ |
| 3.4 to 4.0 (m) | 5H other CH$_2$'s and $\phi$-CH—C $\parallel$ O |
| 2.8 to 3.2 (m) | 6H |
| 7.51 (m) | 2H |
| 7.68 (d) | 1H aromatic protons |
| 7.31 (m) | 1H |
| 8.67 (mobile t.) | N—H—CH$_2$ |
| 11.09 (s. 1) | mobile proton |

EXAMPLE 17

(±)
2,3-dihydro-5-[(4-dimethylamino)-butyl]-3-(4-methoxyphenyl)-1,5-benzothiazepin-4(5H)-one (E) 2-butenedioate 9 g of diethyl azodicarboxylate in solution in 150 ml of tetrahydrofuran were added at ambient temperature over 15 minutes to a solution of 13.8 g of triphenyl phosphine in 350 ml of tetrahydrofuran and the mixture was stirred for 10 minutes. Then, 10 g of 2,3-dihydro-3-(4-methoxyphenyl)-1,5-benzothiazepin-4(5H)-one of Step D of Example 1 were added over 3 minutes followed by stirring for 10 minutes. Then, 6 g of dimethylaminobutanol were added and after 5 hours of stirring at ambient temperature, the tetrahydrofuran was evaporated off. Extraction was done with 2N hydrochloric acid and the extracts were washed with ethyl acetate. The combined aqueous phases were alkalinized with sodium hydroxide. The mixture was extracted with methylene chloride and the organic phase was washed with an aqueous solution of sodium chloride, dried and evaporated to dryness to obtain 5.7 g of crude product which was chromatographed on silica (eluant: methylene chloride-methanol 90-10) to obtain 2 g of the expected product in the form of a base which was taken up in isopropanol. 0.6 g of fumaric acid were added to obtain 1.35 g of the expected product melting at 144° C., after crystallization from isopropanol or from acetonitrile.

Analysis: $C_{26}H_{32}O_6N_2S$: Calculated: %C, 62.38; %H, 6.44; %N, 5.59; %S, 6.40. Found: %C, 62.4; %H, 6.2; %N, 5.7; %S, 6.3.

EXAMPLE 18

(±)
2,3-dihydro-5-[2-[[2-(3,4-dimethoxyphenyl)-ethyl]-methylamino]-ethyl]-3-(4-methoxyphenyl)-1,5-benzothiazepin-4(5H)-one ethanedioate 800 mg of 2,3-dihydro-5-(2-chloroethyl)-3-(4-methoxyphenyl)-1,5-benzothiazepin-4(5H)-one of Step D in Example 14 and 1.6 g of 3,4-dimethoxy-α-phenethyl methylamine were stirred for 5 minutes at 140° C. and the solution was cooled, taken up in methylene chloride, washed with a saturated aqueous solution of sodium bicarbonate, dried and evaporated to dryness under reduced pressure to obtain 2.25 g of crude product which was chromatographed on silica (eluant: methylene chloride-methanol 9-1) to obtain 900 mg of the expected product in the form of a base. The latter was dissolved in 9 ml of methanol and 223 mg of oxalic acid were added. The mixture was heated and after 40 ml of isopropanol were added. The mixture was concentrated to 20 ml. Crystallization was started and left for 4 hours at ambient temperature and separated to obtain 550 mg of the expected product melting at 180° to 190° C. after crystallization from methanol and isopropanol, then from methanol and ether.

Analysis: $C_{31}H_{36}N_2O_8S$: Calculated: %C, 62.40; %H, 6.08; %N, 4.70; %S, 5.37. Found: %C, 62.2; %H, 6.1; %N, 4.6; %S, 5.4.

EXAMPLE 19

(±) 2,3-dihydro-5-[2-(dimethylamino)-ethyl]-3-(3-methoxyphenyl)-1,5-benzothiazepin-4(5H)-one ethanedioate 1.04 of diethyl azodicarboxylate in solution in 3 ml of tetrahydrofuran were added over 10 minutes at ambient temperature to a suspension of 1.43 g of 2,3-dihydro-3-(3-methoxyphenyl)-1,5-benzothiazepin-4(5H)-one, 25 ml of tetrahydrofuran, 535 mg of dimethylamino ethanol and 1.57 g of triphenylphosphine. The mixture was left to return to ambient temperature, then stirred for 24 hours. The tetrahydrofuran was evaporated off and 30 ml of 2N hydrochloric acid were added. Extraction was done with ethyl acetate and the extracts were washed again with hydrochloric acid. The combined aqueous phases were cooled to 4° C. and alkalinized with sodium hydroxide and extraction was done with ethyl acetate. The extracts were washed with water, dried and evaporated to dryness under reduced pressure to obtain 1.6 g of crude product which was chromatographed on silica (eluant: cyclohexane-dioxane 60-40) to obtain 1.05 g of expected product in the form of a base (Rf=0.10) which was dissolved in 20 ml of isopropanol. 371 mg of oxalic acid in solution in methanol were added and partial concentration was carried out. Crystallization was started and after separation, 1.2 g of expected product melting at 208° C. after crystallization from ethanol were obtained.

Analysis: $C_{20}H_{24}N_2O_2S$, $C_2H_2O_4$ (product dried at 150° C.): Calculated: %C, 59.18; %H, 5.87; %N, 6.27; %S, 7.18. Found: %C, 59.3; %H, 5.9; %N, 6.3; %S, 7.0.

The 2,3-dihydro-3-(3-methoxyphenyl)-1,5-benzothiazepin 4(5H)-one used in Example 19 was prepared as follows:

STEP A: Dimethyl (3-methoxyphenyl)-propanedioate 1.48 g of sodium in 50 ml of methanol was stirred until a solution was obtained and after concentrating to dryness, 40 ml of toluene were added, followed by evaporation to dryness. The 100 ml of ethyl ether were added followed by a solution of 9 g of 3-methoxyphenyl acetate and 9 g of dimethyl oxalate in 65 ml of ethyl ether over 15 minutes at ambient temperature. The suspension was stirred for 21 hours at 50° C. and then cooled to +5° C. 100 ml of ether were added and acidified with 2N hydrochloric acid. 50 ml of water were added and the solution was extracted with ether. The extracts were washed with 2N hydrochloric acid and then with a saturated aqueous solution of sodium chloride, dried and concentrated to dryness under reduced pressure to obtain 13 g of the expected product which was used as is for the following step.

STEP B: Methyl 3-methoxy-α-methylene benzene acetate 10.8 ml of 37% formaldehyde in water, 8.2 g of potassium carbonate and 5 mg of hydroquinone were added to 11 g of the product of Step A in suspension in 100 ml of water. After stirring for 2 hours at ambient temperature, extraction was effected with ethyl acetate. The extracts were washed with water, dried and evaporated to dryness under reduced pressure to obtain 9.6 g of the expected product which was used as is for the following step.

STEP C: 3-methoxy-α-methylene benzene acetic acid 4.82 g of potassium hydroxide pellets in 121 ml of water were stirred with 9.60 g of the product of Step B in 121 ml of tetrahydrofuran for 5 hours at ambient temperature. The tetrahydrofuran was evaporated off, and extraction was done with ethyl acetate. The extracts were washed with water and the combined aqueous phases were acidified with concentrated hydrochloric acid. Extraction was carried out again with ethyl acetate and the extracts were washed with water, dried and concentrated to dryness under reduced pressure to obtain 9.2 g of the expected product which was used as is for the following step.

STEP D: α-[[(2-aminophenyl)-thio]-methyl]-3-methoxy-benzeneacetic acid 7.6 ml of aminothiophenol were added to a solution of 8.9 g of the product of Step C and 130 ml of ethanol and the solution was stirred for 90 minutes at 95° C. and left to return to ambient temperature. The ethanol was eliminated under reduced pressure and 50 ml of isopropyl ether were added. Crystallization was started to obtain 7.2 of the expected product which was separated off and dried at 80° C. under reduced pressure. After chromatography of the mother liquors on silica (eluant: ethyl acetate-cyclohexane 1-1), 710 mg of pure product were obtained (Rf=0.16) which after crystallization from ether melted at 128° C.

Analysis: $C_{16}H_{17}NO_3S$: Calculated: %C, 63.35; %H, 5.65; %N, 4.62; %S, 10.57. Found: %C, 63.5; %H, 5.5; %N, 4.5; %S, 10.6.

STEP E: 2,3-dihydro-3-(3-methoxyphenyl)-1,5-benzothiazepin-4(5H)-one 4.60 g of 1-ethyl-3-(3-dimethylaminopropyl)-carbodiimide hydrochloride were added at 10° C. over 2 minutes to 3.64 g of the product of Step D suspended in 110 ml of methylene chloride and the mixture was stirred for 30 minutes at ambient temperature. 100 ml of water were added, and extraction was carried out with methylene chloride. The extracts were washed with water, dried, treated with activated charcoal, filtered, and the solvents were eliminated under reduced pressure to obtain 3.55 g of crude product which was crystallized from ethyl acetate to obtain 3.10 g of expected product melting at 198° C. after crystallization from ethanol.

Analysis: $C_{16}H_{15}NO_2S$: Calculated: %C, 67.35; %H, 5.30; %N, 4.91; %S, 11.24. Found: %C, 67.6; %H, 5.1; %N, 4.7; %S, 11.3.

EXAMPLE 20

(±) 2,3-dihydro-5-(2-(dimethylamino)-ethyl)-3-(4-trifluoromethyl)-phenyl)-1,5-benzothiazepin-4(5H)-one ethanedioate 3.12 g of 2,3-dihydro-3-[4-(trifluoromethyl)-phenyl]-1,5-benzothiazepin-4(5H)-one, then 1.25 g of dimethylaminoethanol were added all at once to a solution of 3.8 g of triphenylphosphine in 100 ml of tetrahydrofuran and the mixture was stirred for 5 minutes. Then, a solution of 2.52 g of diethyl azodicarboxylate in 50 ml of tetrahydrofuran was added over 10 minutes at ambient temperature and after agitation for 23 hours at ambient temperature, the tetrahydrofuran was evaporated off. 13 g of crude product were chromatographed on silica (eluant: methanol-methylene chloride 10-90) to obtain 2.2 g of the expected product in the form of a base which was dissolved in 60 ml of isopropanol. 0.7 ml of oxalic acid in solution in 20 ml of methanol were added and partial concentration was carried out. Crystallization was started and left for 4 hours, followed by separating, rinsing with isopropanol and drying under reduced pressure at 100° C. to obtain 2.1 g of expected product melting at 179° C. after crystallization from isopropanol.

Analysis: $C_{22}H_{23}F_3N_2O_5S$: Calculated: %C, 54.54; %H, 4.78; %f, 11.76; %N, 5.78; %S, 6.62. Found: %C, 54.2; %H, 4.7; %f, 11.5; %N, 5.7; %S, 6.8.

The 2,3-dihydro-3-[4-trifluoromethyl)-phenyl]-1,5-benzothiazepin-4(5H)-one used at the start was prepared as follows:

STEP A:

α-[[(2-aminophenyl)-thio]-methyl]-4-(trifluoromethyl)-benzene acetic acid.

20.41 g of aminothiophenol were added all at once to a solution of 43 g of α-methylene-4-(trifluoromethyl)-benzene acetic acid [J. Med. Chem. (1969), Vol. 12 (3), p. 477 to 480] in 300 ml of ethanol, and the mixture was refluxed for 2 hours. The ethanol was evaporated off and the residue was taken up in 600 ml of ethyl ether and partially concentrated to 300 ml. 200 ml of isopropyl ether were added with concentration to 100 ml and cooled for 30 minutes in ice-cooled water. The crystallized product was separated off, washed with isopropyl ether and dried under reduced pressure at 100° C. to obtain 21.9 g of expected product melting at approx. 138° C.

STEP B:

2,3-dihydro-3-[4-(trifluoromethyl)-phenyl]-1,5-benzothiazepin-4(5H)-one 1.74 g of 1-ethyl-3-(3-dimethylaminopropyl)-carbodiimide were added to 1.55 g of the product of Step A suspended in 25 ml of methylene chloride and the mixture was stirred for 30 minutes. 50 ml of methylene chloride were added, followed by washing with water, and extraction with methylene chloride. The organic phase was dried and concentrated to dryness under reduced pressure to obtain 1.25 g of expected product which after crystallization from isopropanol melted at 195° C.

PHARMACOLOGICAL STUDY

1) Anti-arhythmic action in the rat

Male rats weighing 300–350 g, anaesthetized by intraperitoneal route using 1.20 g/kg of urethane, were tracheotomized and subjected to artificial respiration (40–50 insufflations of 3 ml/minute). Needles were implanted subcutaneously to record the electro-cardiogram of the rats on the signal in the DII derivation. The products under test were administered by intravenous route or by oral route. After five minutes in the case of administration intravenously and one hour in the case of oral administration, the jugular vein of the rats was perfused with 10 micrograms/min. under 0.2 ml of an aconitine solution. The time taken for the first ventricular extrasystoles to appear was noted and the amount of aconitine perfused was calculated, then expressed as a function of the body weight of the animal.

The percentage of increase of the aconitine dose necessary to initiate the ventricular extrasystoles after treatment was calculated relative to the control animals. The results which appear in the table below show that the products of the present Application are endowed with remarkable anti-arhythmic properties.

| Product of Example | Route | Dose mg/kg | Percentage of increase of the aconitine dose for initiating the extrasystoles |
|---|---|---|---|
| 11 | IV | 5 | 32 |
|    | O  | 25 | 135 |
| 13 | IV | 5 | 24 |
|    | O  | 25 | 35 |
| 6  | IV | 5 | 142 |
|    | O  | 25 | >188 |
| 7  | IV | 5 | 25 |
|    | O  | 25 | 129 |

2) Test for the Activity of Anti-Aggregation of Blood-Platelets. Blood-Platelet Aggregation, In Vitro, on Plasma Rich in Blood-Platelets (PRP)

Measurement of blood-platelet aggregation was made by the turbidimetric method of Born et al 1963, J. Physiol., Vol. 168, p. 178. Rabbit's blood was removed on Na citrate at 3.2% by cardiac puncture and the plasma rich in blood-platelets was obtained by centrifuging and adjustment of the number of blood-platelets to 300,000 per microliter. The aggregation was induced by collagen (40 micrograms per ml of PRP) or PAF acether (0.05 micromoles per liter of PRP). The compounds under test were incubated at different concentrations in the PRP 2 minutes before the aggregating agent. The results were expressed in $IC_{50}$ (concentration inhibiting the aggregation by 50% relative to the control curves).

| Product of Example | $IC_{50}$ in $10^{-5}$ moles per liter | |
|---|---|---|
|  | Induction by collagen | Induction by PAF-ACETHER |
| 11 | 0.8 | 4 |
| 12 | 5.6 | 0.9 |
| 1 | 7.4 | 7.8 |
| 9 | 6.6 | 5.8 |

3) Test for Anti-Serotoninergic Activity

Broncho-constriction in a guinea-pig induced by serotonin.

The pulmonary resistance to insufflation was measured by the technique of "overflow" according to KONZETT et al [Arch. Ex. Pathol. Pharmakol, 1940, Vol. 195, p. 71]. The guinea-pigs were anaesthetized with urethane and the jugular vein was catherized to inject the products, and the trachea was catheterized to insert artificial ventilation. Broncho-constriction was induced by a dose of 3 to 5 micrograms/kg of serotonin injected intravenously and the antagonists were injected one minute before the induction of the bronchospasm. It can be noted from the results of the table below that the products of the present Application have a strong anti-serontoninergic activity.

| Product of | Dose mg/kg | Percentage of inhibition of the broncho-constriction |
| --- | --- | --- |
| 11 | 1 | 82 |
| 12 | 1 | 64 |
| 13 | 1 | 87 |
| 1 | 1 | 79 |
| 5 | 1 | 87 |

4) Study of the Acute Toxicity

The lethal doses LD of the various compounds under test were evaluated after a single administration intraperitoneally or orally to a mouse. The maximum dose which did not cause any deaths over 8 days was called $LD_0$.

The following results were obtained:

| Product of Example | $LD_0$ in mg/kg | |
| --- | --- | --- |
| | IP | O |
| 11 | 80 | 100 |
| 12 | 100 | >200 |
| 13 | 80 | >200 |
| 6 | 100 | 100 |
| 7 | 100 | 100 |

Various modifications of the compounds and method of the invention may be made without departing from the spirit or scope thereof and it is to be understood that the invention is intended to be limited only as defined in the appended claims.

What we claim is:

1. A compound selected from the group consisting of all possible isomeric forms, racemic or optically active of a compound of the formula

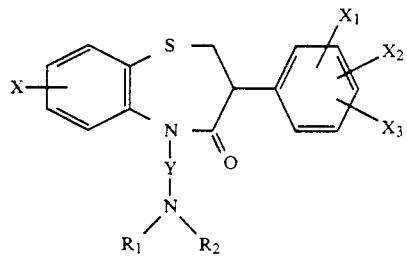

wherein X is selected from the group consisting of hydrogen, halogen, —OH, alkyl and alkoxy of 1 to 3 carbon atoms, —NO$_2$, —NH$_2$, —CF$_3$ and alkylamino and dialkylamino of 1 to 4 alkyl carbon atoms, X$_1$, X$_2$ and X$_3$ are individually selected from the group consisting of hydrogen, halogen, —OH, alkyl and alkoxy of 1 to 3 carbon atoms, —NO$_2$, —CF$_3$, —SCF$_3$, —OCF$_3$, —NH$_2$ and alkylamino and dialkylamino of 1 to 4 alkyl carbon atoms, Y is

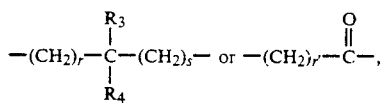

r and s are integers from 0 to 4 with r+s=1 to 4, R$_3$ and R$_4$ are individually hydrogen or alkyl of 1 to 4 carbon atoms, r' is an integer from 1 to 4, R$_1$ and R$_2$ are individually selected from the group consisting of hydrogen, alkyl of 1 to 4 carbon atoms unsubstituted or substituted with aryl of 6 to 12 carbon atoms optionally substituted with 1 to 3 members of the group consisting of alkyl and alkoxy of 1 to 4 carbon atoms, —OH, —CN, halogen, —NH$_2$ and alkylamino and dialkylamino of 1 to 4 alkyl carbon atoms or R$_1$ and R$_2$ together with the nitrogen to which they are attached form a member selected from the group consisting of pyrrolidinyl, imidazolidinyl, pyrazolidinyl, piperidyl, piperazinyl or morpholinyl, all optionally substituted on a carbon of the heterocycle or on the nitrogen atom when the heterocycle contains a second nitrogen atom by alkyl of 1 to 4 carbon atoms or by aryl or arylalkyl of 6 to 12 carbon atoms optionally substituted with 1, 2 or 3 members of the group consisting of halogen and alkyl or alkoxy of 1 to 4 carbon atoms and their non-toxic, pharmaceutically acceptable acid addition salts, with the proviso that at least one of X, X$_1$, X$_2$ and X$_3$ is selected from the group consisting of —OH, —NH$_2$, alkylamino and dialkylamino of 1 to 4 alkyl carbon atoms or at least one of X$_1$, X$_2$ and X$_3$ is selected from the group consisting of —SCF$_3$ or —OCF$_3$.

2. A compound of claim 1 wherein X is hydrogen.

3. A compound of claim 1 wherein R$_1$ and R$_2$ are individually methyl, ethyl or isopropyl.

4. A compound of claim 1 wherein R$_1$ is —CH$_3$ and R$_2$ is phenethyl optionally mono or di substituted with methyl or methoxy.

5. A compound of claim 1 wherein R$_1$ is hydrogen and R$_2$ is dialkylamino-methyl or ethyl.

6. A compound of claim 1 wherein R$_1$ and R$_2$ form together with the nitrogen atom to which they are attached a member of the group consisting of pyrrolidinyl, piperidyl, morpholinyl, piperazinyl optionally substituted on the nitrogen atom not linked to the (CH$_2$)s— by alkyl of 1 to 4 carbon atoms or by aryl of 6 to 12 carbon atoms or aralkyl of 6 to 12 carbon atoms optionally substituted by halogen or alkyl or alkoxy of 1 to 4 carbon atoms.

7. A compound of claim 1 wherein X$_3$ is hydrogen and X$_1$ and X$_2$ are individually chlorine or bromine or —OH or —OCH$_3$.

8. A compound of claim 1 wherein Y is

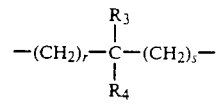

9. A compound of claim 8 wherein r+s=1 or 2 and R$_3$ and R$_4$ are hydrogen.

10. A compound of claim 1 wherein Y is

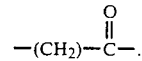

11. A compound selected from the group consisting of (±)-5-[2-(dimethylamino)-ethyl]-2,3-dihydro-3(4-chloro-phenyl)-1,5-benzothiazepin-4(5H)-one,
(±)5-[2-(dimethylamino)-ethyl]-2,3-dihydro-3-(2-methoxy-phenyl)-1,5-benzothiazepin-4(5H)-one,
(±)-5-[2-(dimethylamino)-ethyl]-2,3-dihydro-3-(4-methoxy-phenyl)-1,5-benzothiazepin-4(5H)-one
and their non-toxic, pharmaceutically acceptable acid addition salts.

12. A compound having a formula selected from the group consisting of

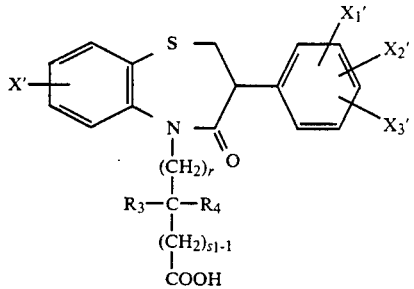

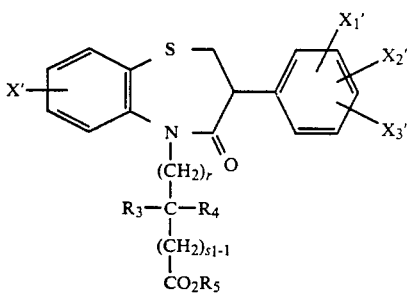

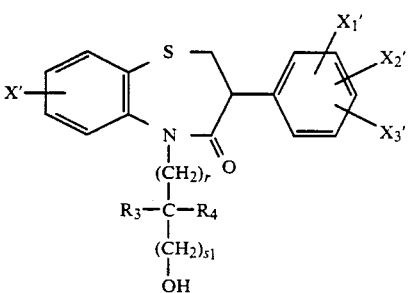

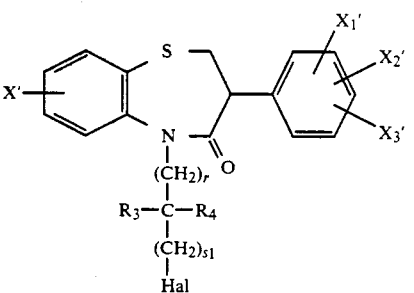

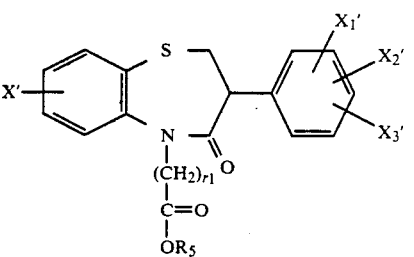

and

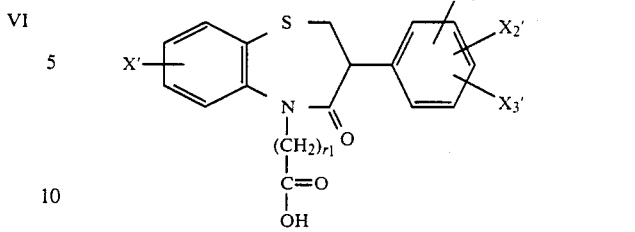

wherein $R_3$, $R_4$, n, s and R have the definitions of claim 1, X', has the definitions of X, and $X'_1$, $X'_2$, $X'_3$ have the definitions of $X_1$, $X_2$ and $X_3$ or are a protected derivative, Hal is halogen and $R_5$ is alkyl of 1 to 5 carbon atoms.

13. An antiarhythmic composition comprising an antiarhythmically effective amount of at least one compound of claim 1 and an inert pharmaceutical carrier.

14. A composition of claim 13 wherein the active compound is selected from the group consisting of
(±)-5-[2-(dimethylamino)-ethyl]-2,3-dihydro-3(4-chloro-phenyl)-1,5-benzothiazepin-4(5H)-one,
(±)5-[2-(dimethylamino)-ethyl]-2,3-dihydro-3-(2-methoxy-phenyl)-1,5-benzothiazepin-4(5H)-one,
(±)-5-[2-(dimethylamino)-ethyl]-2,3-dihydro-3-(4-methoxy-phenyl)-1,5-benzothiazepin-4(5H)-one
and their non-toxic, pharmaceutically acceptable acid addition salts.

15. A method of treating arhythmia in warm-blooded animals comprises administering to warm-blooded animals an anti-arhythmically effective amount of at least one compound selected from the group consisting of all possible isomeric forms, racemic or optically active of a compound of the formula

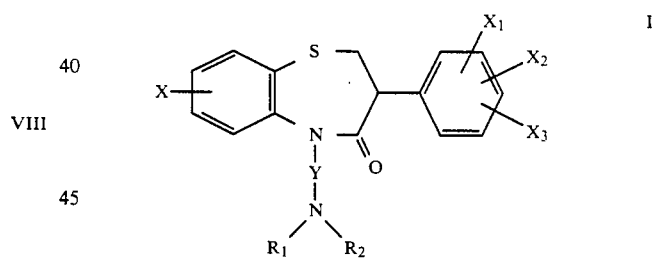

wherein X is selected from the group consisting of hydrogen, halogen, —OH, alkyl and alkoxy of 1 to 3 carbon atoms, —NO$_2$, —NH$_2$, —CF$_3$ and alkylamino and dialkylamino of 1 to 4 alkyl carbon atoms, $X_1$, $X_2$ and $X_3$ are individually selected from the group consisting of hydrogen, halogen, —OH, alkyl and alkoxy of 1 to 3 carbon atoms, —NO$_2$, —CF$_3$, —SCF$_3$, —OCF$_3$, —NH$_2$ and alkylamino and dialkylamino of 1 to 4 alkyl carbon atoms, Y is

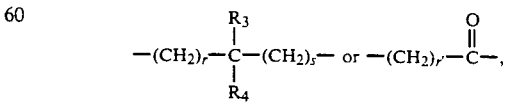

integers from 0 to 4 with r+s=1 to 4, $R_3$ and $R_4$ are individually hydrogen or alkyl of 1 to 4 carbon atoms, r' is an integer from 1 to 4, $R_1$ and $R_2$ are individually selected from the group consisting of hydrogen, alkyl of 1 to 4 carbon atoms unsubstituted or substituted with aryl of 6 to 12 carbon atoms optionally substituted with 1 to 3 members of the group consisting of alkyl and alkoxy of 1 to 4 carbon atoms, —OH, —CN, halogen, —NH$_2$ and alkylamino and dialkylamino of 1 to 4 alkyl carbon atoms or R$_1$ and R$_2$ together with the nitrogen to which they are attached form a member selected from the group consisting of pyrrolidinyl, imidazolidinyl, pyrazolidinyl, piperidyl, piperazinyl or morpholinyl, all optionally substituted on a carbon of the heterocycle or on the nitrogen atom when the heterocycle contains a second nitrogen atom by alkyl of 1 to 4 carbon atoms or by aryl or arylalkyl of 6 to 12 carbon atoms optionally substituted with 1, 2 or 3 members of the group consisting of halogen and alkyl or alkoxy of 1 to 4 carbon atoms and their non-toxic, pharmaceutically acceptable acid addition salts.

16. A method of claim 15 wherein in the compound of formula I X is hydrogen.

17. A method of claim 15 wherein in the compound of formula I R$_1$ and R$_2$ are individually methyl, ethyl or isopropyl.

18. A method of claim 15 wherein in the compound of formula I R$_1$ is —CH$_3$ and R$_2$ is phenethyl optionally mono or di substituted with methyl or methoxy.

19. A method of claim 15 wherein in the compound of formula I R$_1$ is hydrogen and R$_2$ is dialkylamino-methyl or ethyl.

20. A method of claim 15 wherein in the compound of formula I R$_1$ and R$_2$ form together with the nitrogen atom to which they are attached a member of the group consisting of pyrrolidinyl, piperidyl, morpholinyl, piperazinyl optionally substituted on the nitrogen atom not linked to the (CH$_2$)s— by alkyl of 1 to 4 carbon atoms or by aryl of 6 to 12 carbon atoms or aralkyl of 6 to 12 carbon atoms optionally substituted by halogen or alkyl or alkoxy of 1 to 4 carbon atoms.

21. A method of claim 15 wherein in the compound of formula I X$_3$ is hydrogen and X$_1$ and X$_2$ are individually chlorine or bromine or —OH or —OCH$_3$.

22. A method of claim 15 wherein in the compound of formula I Y is

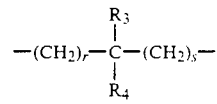

23. A method of claim 15 wherein in the compound of formula I r+s=1 or 2 and R$_3$ and R$_4$ are hydrogen.

24. A method of claim 15 wherein in the compound of formula I Y is

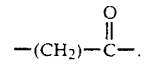

25. A method of claim 13 wherein the active compound is selected from the group consisting of
(±)-5-[2-(dimethylamino)-ethyl]-2,3-dihydro-3(4-chloro-phenyl)-1,5-benzothiazepin-4(5H)-one,
(±)5-[2-(dimethylamino)-ethyl]-2,3-dihydro-3-(2-methoxy-phenyl)-1,5-benzothiazepin-4(5H)-one,
(±)-5-[2-(dimethylamino)-ethyl]-2,3-dihydro-3-(4-methoxy-phenyl)-1,5-benzothiazepin-4(5H)-one
and their non-toxic, pharmaceutically acceptable acid addition salts.

* * * * *

UNITED STATES PATENT AND TRADEMARK OFFICE
CERTIFICATE OF CORRECTION

PATENT NO. : 5,063,225

DATED : Nov. 5, 1991

Page 1 of 2

INVENTOR(S) : Francois Clemence; Daniel Frechet, Gilles Hamon and Simone Jouquey It is certified that error appears in the above-identified patent and that said Letters Patent is hereby corrected as shown below:

Col. Line
35   Claim 1   " 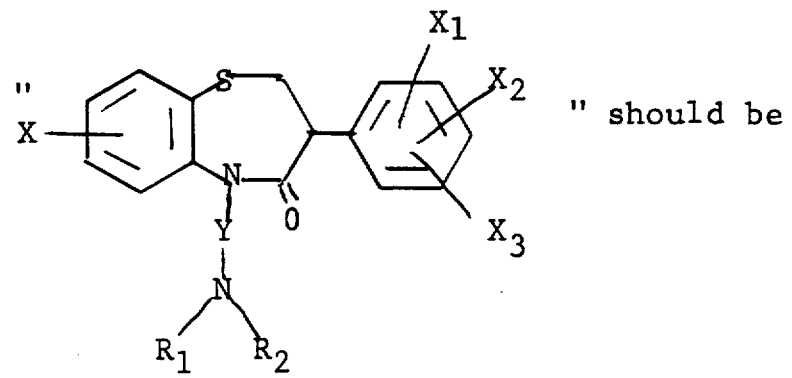 " should be

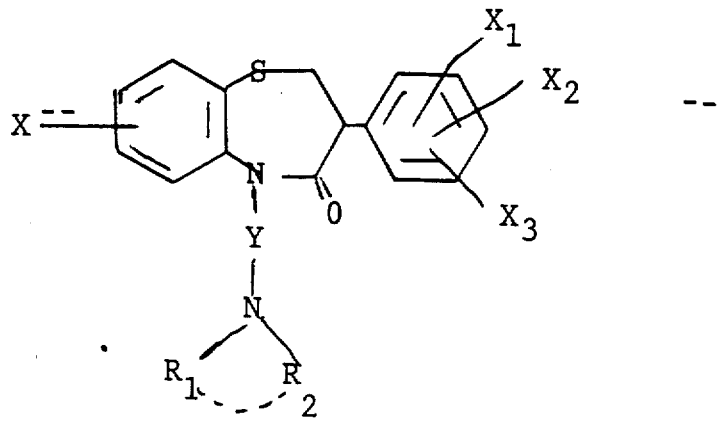 --

UNITED STATES PATENT AND TRADEMARK OFFICE
CERTIFICATE OF CORRECTION

PATENT NO. : 5,063,225

DATED : Nov. 5, 1991

INVENTOR(S) : Francois Clemence, Daniel Frechet, Gilles Hamon and Simone Jouquey It is certified that error appears in the above-identified patent and that said Letters Patent is hereby corrected as shown below:

Col. Line

38 Claim 15  should be

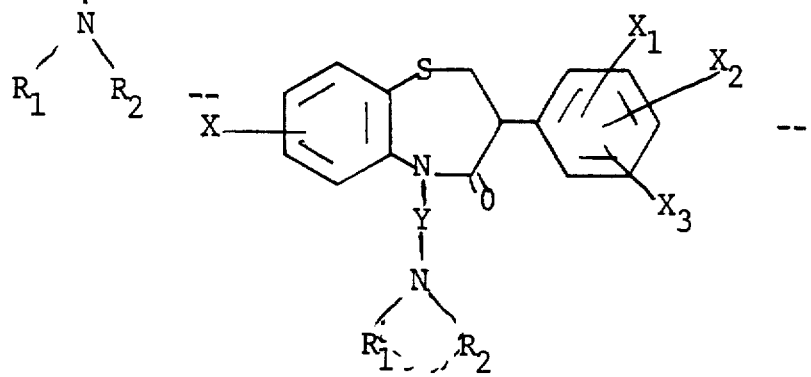

38 Claim 15 Left out ''--r and s are--
Line 60

Signed and Sealed this

Twenty-seventh Day of April, 1993

Attest:

MICHAEL K. KIRK

Attesting Officer  Acting Commissioner of Patents and Trademarks